US010227300B2

(12) United States Patent
Willy et al.

(10) Patent No.: US 10,227,300 B2
(45) Date of Patent: Mar. 12, 2019

(54) SYNTHESIS OF TRIACETONEDIAMINE COMPOUNDS BY REDUCTIVE AMINATION PROCEEDING FROM TRIACETONEDIAMINE AND DERIVATIVES THEREOF

(71) Applicants: Benjamin Willy, Duesseldorf (DE); Jochen Niemeyer, Essen (DE); Guenter Kreilkamp, Marl (DE); Beatrix Vom Bruch, Herten (DE); Manfred Neumann, Marl (DE); Michael Keup, Marl (DE)

(72) Inventors: Benjamin Willy, Duesseldorf (DE); Jochen Niemeyer, Essen (DE); Guenter Kreilkamp, Marl (DE); Beatrix Vom Bruch, Herten (DE); Manfred Neumann, Marl (DE); Michael Keup, Marl (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/004,062

(22) Filed: Jan. 22, 2016

(65) Prior Publication Data

US 2016/0214937 A1    Jul. 28, 2016

(30) Foreign Application Priority Data

Jan. 22, 2015   (EP) .................................... 15152070

(51) Int. Cl.
    *C07D 211/58*   (2006.01)
(52) U.S. Cl.
    CPC .................................. *C07D 211/58* (2013.01)
(58) Field of Classification Search
    None
    See application file for complete search history.

(56) References Cited

U.S. PATENT DOCUMENTS

| 4,110,331 | A | 8/1978 | Pettersson |
| 4,435,572 | A | 3/1984 | Rapoport et al. |
| 4,605,743 | A | 8/1986 | Malz, Jr. et al. |
| 5,130,429 | A | 7/1992 | Piccinelli et al. |
| 5,945,536 | A | 8/1999 | Jegelka et al. |
| 2016/0214962 | A1 | 7/2016 | Niemeyer et al. |

FOREIGN PATENT DOCUMENTS

| CA | 2 060 546 C | 7/2002 |
| CN | 105017131 A | 11/2015 |
| DE | 692 20 708 T2 | 1/1998 |
| EP | 0 047 967 A1 | 3/1982 |
| EP | 0 302 020 A2 | 2/1989 |
| EP | 0 302 020 A3 | 2/1989 |
| EP | 0 319 480 A2 | 6/1989 |
| EP | 0 319 480 A3 | 6/1989 |
| EP | 0 729 947 A1 | 9/1996 |
| EP | 0 857 719 A1 | 8/1998 |
| EP | 0 857 719 B1 | 4/2002 |
| EP | 3 048 097 A1 | 7/2016 |
| GB | 2 047 681 A | 12/1980 |
| WO | WO 2004/089913 A1 | 10/2004 |
| WO | WO 2005/123679 A2 | 12/2005 |
| WO | WO 2008/101979 A1 | 8/2008 |

OTHER PUBLICATIONS

Amine, Wikipedia p. 1-9 (2016).*
Bojinov, Dyes and Pigments, vol. 74, 187-194, 2007. (Year: 2007).*
Xia, Polymer Engineering and Science, 2197-2206, 2014. (Year: 2014).*
European Search Report dated Nov. 10, 2015 in Patent Application 15152070.7 with English translation of categories of cited documents.
Jerzy Zakrzewski, et al., "Efficient Synthesis of 4-Isocyano-2,2,6,6-Tetramethylpiperidine-1-Oxyl" Organic Preparations and Procedures International: The New Journal for Organic Synthesis, vol. 35, No. 4, XP055197816, Aug. 1, 2003, pp. 387-390 and cover page.
C. Harris, "Untersuchungen Über Die Cyclischen Acetonbasen" Justus Liebigs Annalen Der Chemie, vol. 417, XP002741350, 1918, pp. 107-191.
C. Harris, ""Untersuchungen über die cyclischen Acetonbasen, Justus Liebigs Annalen Der Chemie, vol. 417, XP002741350, 1918, 4 Pages (submitting partial English translation only, reference previously filed).
Extended Search Report dated Jun. 13, 2016 in European Patent Application No. 16152152.1 (with English translation of category of cited documents).
J. Kirchhoff et al., "Triacetoneamine Derivatives Industrial Applications and Recent Developments", Addcon World "99—A Two-Day Conference organized by Rapra Technology Limited, Oct. 27 & 28, 1999, Czech Republic, Paper 11, pp. 1-9.
Anita H. Lewin, et al., "Molecular Features Associated with Polyamine Modulation of NMDA Receptors", Journal of Medicinal Chemistry, vol. 41, No. 6, 1998, pp. 988-995.
Ana Minatti, et al., "Synthesis of Chiral 3-Substituted Indanones via an Enantioselective Reductive-Heck Reaction", J. Org. Chem., vol. 72, No. 24, 2007, pp. 9253-9258.
Ihor E. Kopka, et al., "Preparation of a Series of Highly Hindered Secondary Amines, Including Bis(triethylcarbinyl)amine", J. Org. Chem., vol. 45, No. 23, 1980, pp. 4616-4622.

(Continued)

*Primary Examiner* — D Margaret M Seaman
(74) *Attorney, Agent, or Firm* — Oblon, McClelland, Maier & Neustadt, L.L.P.

(57) ABSTRACT

An N-substituted triacetonediamine compound is prepared by reacting 4-amino-2,2,6,6-tetramethylpiperidine or a derivative thereof with a carbonyl compound in a reductive amination, wherein reductive conditions are established by conducting the reaction in the presence of hydrogen and in the presence of a supported catalyst, wherein the supported catalyst includes at least one metal M, wherein the metal M is selected from the group consisting of V, Cr, Mo, Mn, Ni, Pd, Pt, Fe, Ru, Os, Co, Rh, Ir, and Cu.

14 Claims, No Drawings

(56) References Cited

OTHER PUBLICATIONS

Wilson B. Lutz, et al., "New Derivatives of 2,2,6,6-Tetramethylpiperidine", J. Org. Chem., vol. 27, May 1962, pp. 1695-1703.
Extended European Search Report dated Sep. 15, 2017 in Patent Application No. 17178003.4 (with English translation of categories of cited documents).
Nerozzi, "Heterogeneous Catalytic Hydrogenation", Platinum Metals Rev. 56(4):236-241 (2012).
Nishimura, Handbook of Heterogeneous Catalytic Hydrogenation for Organic Synthesis, Wiley, New York (2001), pp. 1-3, 236-237, 241-246.

* cited by examiner

SYNTHESIS OF TRIACETONEDIAMINE COMPOUNDS BY REDUCTIVE AMINATION PROCEEDING FROM TRIACETONEDIAMINE AND DERIVATIVES THEREOF

The present invention relates to a process in which 4-amino-2,2,6,6-tetramethylpiperidine ("triacetonediamine"; TAD) or a 4-amino-2,2,6,6-tetramethylpiperidinyl group is reacted with a carbonyl compound in a reductive amination. The process according to the invention is especially suitable for preparation of derivatives of TAD.

BACKGROUND OF THE INVENTION

1. Field of the Invention

The group of the "hindered amine light stabilizers (HALS)" is used for stabilization of polyolefins, for example polyethylene and polypropylene, against the effect of outside influences, for example UV light and high temperatures. The HALS derivatives contain, as functional unit, a 2,2,6,6-tetramethylpiperidinyl group which is fundamental to the stabilizing action. The stabilizing action is characterized in that, for example, the optical or mechanical properties of the stabilized polymer are preserved for longer compared to the unstabilized polymer, and so, for example, a process of polymer yellowing is slowed down.

2. Discussion of the Background

The introduction of the 2,2,6,6-tetramethylpiperidinyl group is generally effected by using 2,2,6,6-tetramethyl-4-piperidinone (triacetonamine; TAA) as reactant in the synthesis reaction. The conversion of TAA is usually effected by reductive amination, i.e. by reaction with an amine under reductive conditions, giving the corresponding derivatives of 4-amino-2,2,6,6-tetramethylpiperidine. These are then used as HALS either directly or after further chemical modifications.

The preparation of derivatives of TAD by reductive amination of TAA with amines is described in the prior art, for example in EP 0 857 719 B1 (as a continuous process) and DE 692 20 708 T2 (as a non-continuous process). What is common to the prior art processes is that TAA is reacted with an amine ($RNH_2$; the R radical is, for example, a hydrocarbyl radical). This affords an imine intermediate which reacts in the presence of molecular hydrogen, by means of reductive amination over a noble metal or base metal catalyst [M] (for example Ru, Pd, Pt, Co, Ni) to give the desired target product. This involves employing high (EP 0 857 719 B1) or low (DE 692 20 708 T2) partial hydrogen pressures, and the corresponding TAD derivative is obtained.

The reaction scheme <1> according to these conventional methods can be summarized as follows (where R and [M] are as defined above):

<1>

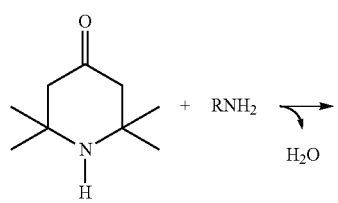

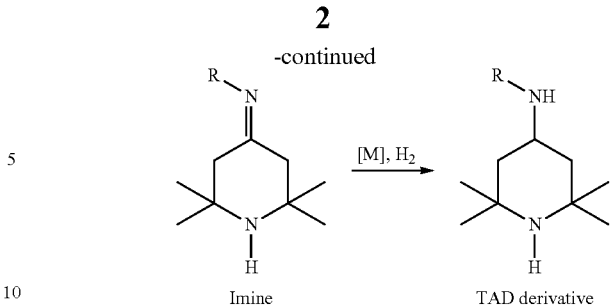

Imine          TAD derivative

Specifically the process described in EP 0 857 719 B1 gives high yields of N-substituted TAD derivatives with a purity of >99% in some cases. However, this process (and of course also that described in DE 692 20 708 T2) is based on TAA as reactant, and a certain residual content of TAA in the end product is unavoidable as a result.

This results in a crucial disadvantage, especially in the case of use of the TAD derivatives prepared by the prior art processes. When these TAD derivatives obtained in this way, or conversion products thereof, are used as stabilizing additives for polyolefins, it is disadvantageous when the additives themselves lead to discolouration of the material. It is particularly disadvantageous here that TAA in the presence of oxygen forms highly coloured breakdown products which greatly impair the quality of the plastics with regard to the colour properties thereof. Even traces of TAA in the end product lead to noticeable discolouration of the material over time.

Complete avoidance or at least the furthest possible reduction in any residual content of TAA is therefore important in the case of use of light stabilizers having 2,2,6,6-piperidinyl substituents. This cannot be achieved by the prior art processes per se, since they inevitably proceed from TAA as reactant.

In addition, the use of TAA as raw material results in further disadvantages which are manifested particularly in plants on the industrial scale. For instance, TAA is a solid at room temperature and does not melt until ~35° C. This requires additional apparatus complexity and energy expenditure in order to convert TAA to a processible state.

In addition, preparation of TAD derivatives disubstituted at the exocyclic nitrogen atom by reductive amination is possible only with a very small conversion, if at all, by the prior art processes. Such disubstituted TAD derivatives are also of interest as light stabilizers.

SUMMARY OF THE INVENTION

The problem addressed by the present invention was thus that of providing a process for preparing TAD compounds which does not have the above-described disadvantages. More particularly, the process should enable the preparation of TAD compounds having higher colour stability and make available a wider range of TAD compounds.

A process which solves the problem described has now surprisingly been found.

The present invention relates to a process for preparing an N-substituted triacetonediamine compound by reacting 4-amino-2,2,6,6-tetramethylpiperidine or a derivative thereof with a carbonyl compound in a reductive amination, wherein reductive conditions are established by conducting the reaction in the presence of hydrogen and in the presence of a supported catalyst, wherein the supported catalyst includes at least one metal M, wherein the metal M is selected from the group consisting of V, Cr, Mo, Mn, Ni, Pd, Pt, Fe, Ru, Os, Co, Rh, Ir, and Cu.

DETAILED DESCRIPTION OF THE INVENTION

Brief Description of the Invention

The present invention relates, in a first aspect, to a process according to the following Points 1.1 to 1.15:

1.1 Process for preparing an N-substituted triacetonediamine compound,
characterized in that at least one triacetonediamine compound (I) is reacted with at least one carbonyl compound (II) under reductive conditions,
where the triacetonediamine compound (I) is selected from the group consisting of the chemical structures (I-A), (I-B), (I-C), (I-D), (I-E) with

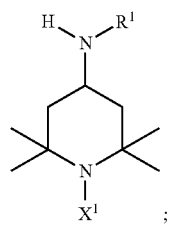
(I-A)

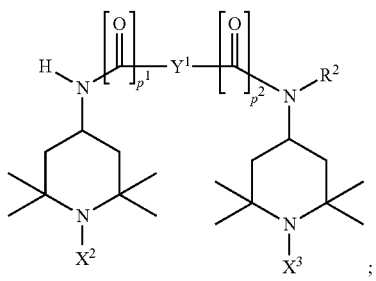
(I-B)

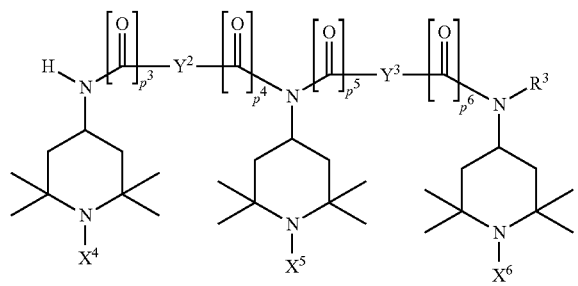
(I-C)

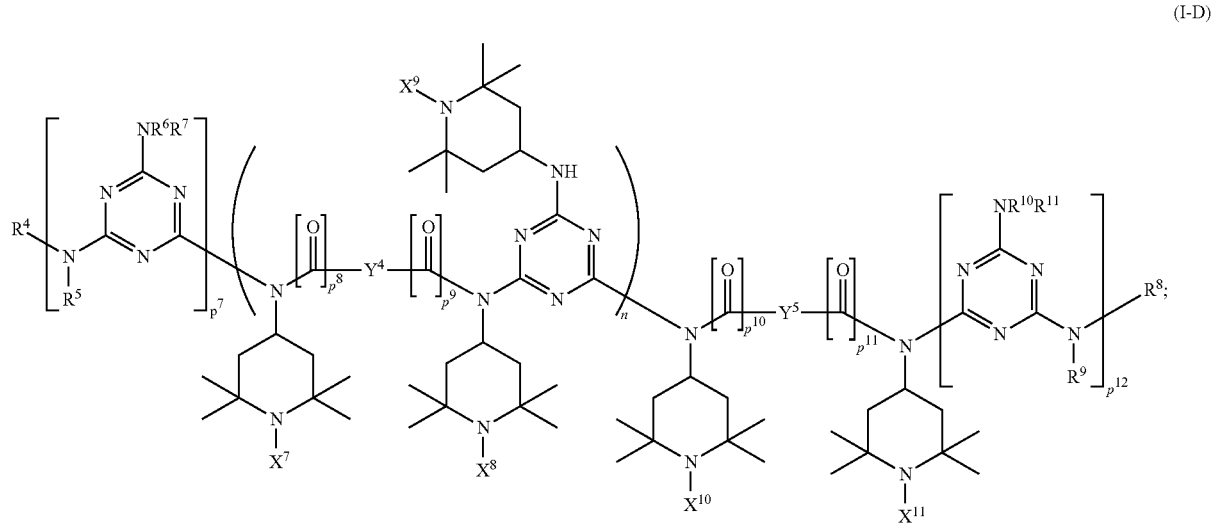
(I-D)

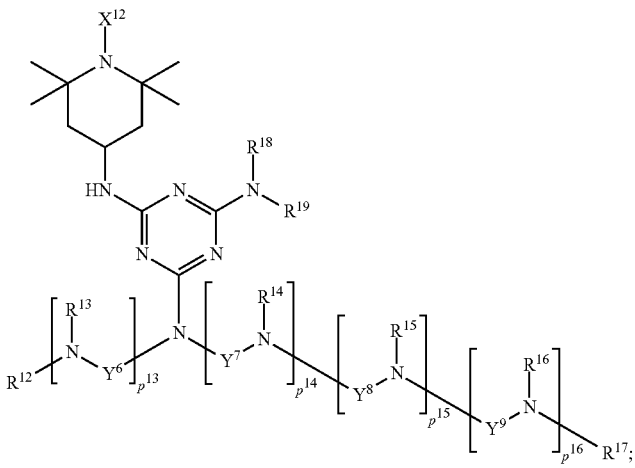

(I-E)

where n is an integer from the range of 1 to 20;
where $p^1, p^2, p^3, p^4, p^5, p^6, p^7, p^8, p^9, p^{10}, p^{11}, p^{12}, p^{13}, p^{14}, p^{15}, p^{16}$ are each independently 0 or 1;
where $X^1, X^2, X^3, X^4, X^5, X^6, X^7, X^8, X^9, X^{10}, X^{11}, X^{12}$ are each independently selected from the group consisting of hydrogen, OH, —O., unbranched or branched alkyl group having 1 to 10 carbon atoms, unbranched or branched alkoxy group having 1 to 10 carbon atoms;
where $Y^1, Y^2, Y^3, Y^4, Y^5, Y^6, Y^7, Y^8, Y^9$ are each independently selected from the group consisting of
unbranched or branched alkylene group having 1 to 30 carbon atoms,
divalent saturated hydrocarbyl group having 3 to 30 carbon atoms and having at least one saturated ring composed of 3 to 30 carbon atoms,
divalent hydrocarbyl group having 6 to 30 carbon atoms, of which at least 6 carbon atoms are present in an aromatic system and the other carbon atoms, if present, are saturated,
a bridging radical having a chemical structure selected from the group consisting of (i), (ii) with (i)

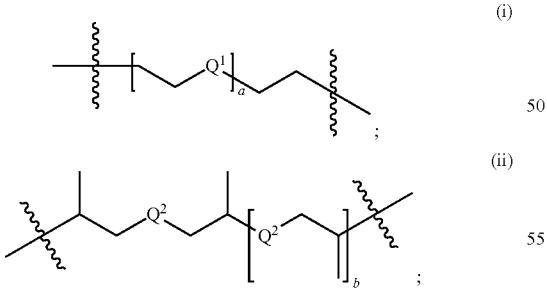

(ii)

where
  $Q^1, Q^2$ are each independently selected from the group consisting of —O—, —S—, —NH— and —NR'— with R'=unbranched or branched alkyl group having 1 to 6 carbon atoms,
  where a is an integer selected from the range of 1 to 50,
  where b is an integer selected from the range of 0 to 50,
and where $Y^1$ may also be a direct bond if at least one of $p^1$ and $p^2$ has the value of 1,
and where $Y^2$ may also be a direct bond if at least one of $p^3$ and $p^4$ has the value of 1,
and where $Y^3$ may also be a direct bond if at least one of $p^5$ and $p^6$ has the value of 1,
and where $Y^4$ may also be a direct bond if at least one of $p^8$ and $p^9$ has the value of 1,
and where $Y^5$ may also be a direct bond if at least one of $p^{10}$ and $p^{11}$ has the value of 1;
where the $R^1, R^2, R^3, R^4, R^5, R^6, R^7, R^8, R^9, R^{10}, R^{11}$ radicals are each independently selected from the group consisting of
hydrogen,
unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$),
unbranched or branched acyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$);
a radical having a chemical structure selected from the group consisting of (iii), (iv), (v), (vi), (vii), (viii), (ix) with

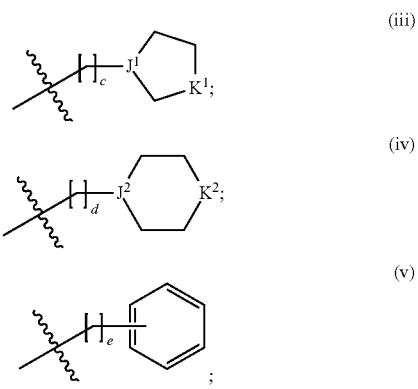

-continued

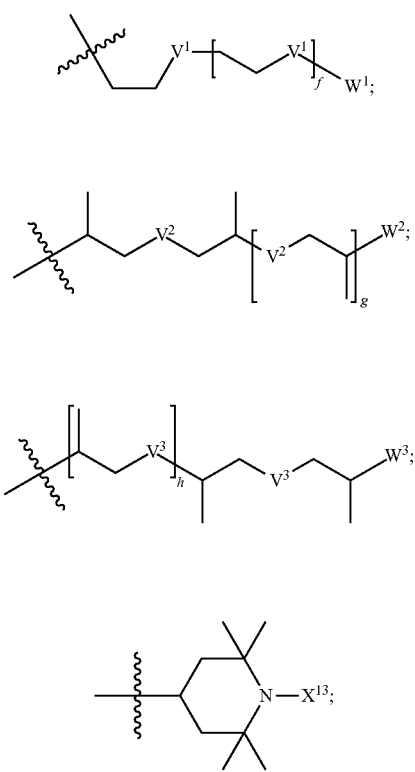

(vi)

(vii)

(viii)

(ix)

where J¹, J² are each independently selected from the group consisting of CH, N, where K¹, K² are each independently selected from the group consisting of —O—, —NH—, —N(CH$_3$)—, —N(CH$_2$CH$_3$)—, —S—, —CH$_2$—, where V¹, V², V³ are each independently selected from the group consisting of —O—, —S—, —NH—, —NR″— with R″=unbranched or branched alkyl group having 1 to 6 carbon atoms, where W¹, W², W³ are each independently selected from the group consisting of H, methyl, ethyl, where c, d, e, f, g, h are each independently an integer from the range of 0 to 50, where X¹³ is selected from the group consisting of hydrogen, —OH, —O., unbranched or branched alkyl group having 1 to 10 carbon atoms, unbranched or branched alkoxy group having 1 to 10 carbon atoms, where, in the chemical structures (iii), (iv), (v), (vi), (vii), (viii), (ix), at least one hydrogen radical bonded to a carbon atom may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$);

where the R¹², R¹³, R¹⁴, R¹⁵, R¹⁶, R¹⁷ radicals are each independently selected from the group consisting of hydrogen, unbranched or branched alkyl group having 1 to 30 carbon atoms, a group having the chemical structure (x) with

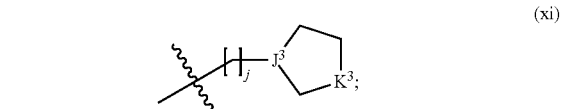

(x)

where the R¹⁸, R¹⁹, R²⁰, R²¹, R²², R²³ radicals are each independently selected from the group consisting of hydrogen, unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$), unbranched or branched acyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$), a radical having a chemical structure selected from the group consisting of (xi), (xii), (xiii), (xiv), (xv), (xvi), (xvii) with

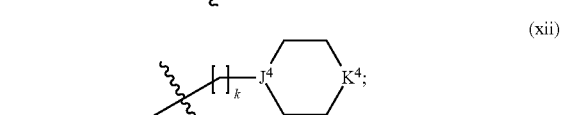

(xi)

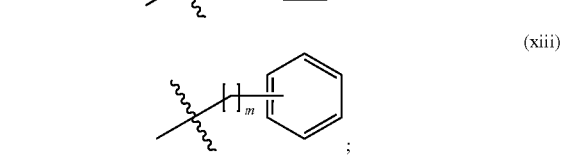

(xii)

(xiii)

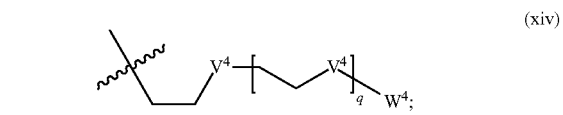

(xiv)

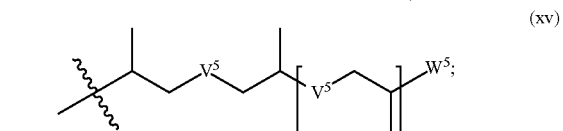

(xv)

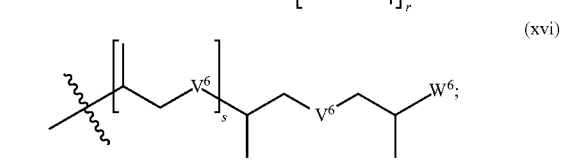

(xvi)

-continued

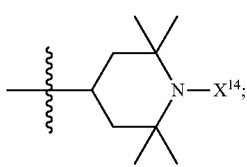
(xvii)

where J³, J⁴ are each independently selected from the group consisting of CH, N,
where K³, K⁴ are each independently selected from the group consisting of —O—, —NH—, —N(CH₃)—, —N(CH₂CH₃)—, —S—, —CH₂—,
where V⁴, V⁵, V⁶ are each independently selected from the group consisting of —O—, —S—, —NH—, —NR'''— with R'''=unbranched or branched alkyl group having 1 to 6 carbon atoms,
where W⁴, W⁵, W⁶ are each independently selected from the group consisting of H, methyl, ethyl,
where j, k, m, q, r, s are each independently an integer from the range of 0 to 50,
where $X^{14}$ is selected from the group consisting of hydrogen, —OH, —O., unbranched or branched alkyl group having 1 to 10 carbon atoms, unbranched or branched alkoxy group having 1 to 10 carbon atoms,
where, in the chemical structures (xi), (xii), (xiii), (xiv), (xv), (xvi), (xvii), at least one hydrogen radical bonded to a carbon atom may be replaced by a radical selected from the group consisting of —OH, —NH₂, —OCH₃, —OCH₂CH₃, —NH(CH₃), —N(CH₃)₂, —NH(CH₂CH₃), —N(CH₂CH₃)₂, —N(CH₃)(CH₂CH₃),
and with the proviso that $R^{12}$ and $R^{17}$, when $p^{13}=p^{14}=p^{15}=p^{16}=0$, may each independently also be a group of the chemical structure (xviii) with

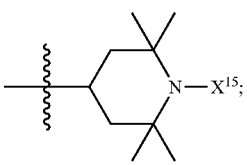
(xviii)

where $X^{15}$ is selected from the group consisting of hydrogen, —OH, —O., unbranched or branched alkyl group having 1 to 10 carbon atoms, unbranched or branched alkoxy group having 1 to 10 carbon atoms;
and where the carbonyl compound (II) is selected from the group consisting of the chemical structures (II-A), (II-B), (II-C) with

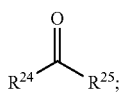
(II-A)

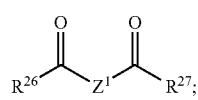
(II-B)

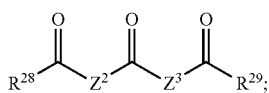
(II-C)

where $Z^1$, $Z^2$, $Z^3$ are each independently selected from the group consisting of
direct bond,
unbranched or branched alkylene group having 1 to 30 carbon atoms,
divalent saturated hydrocarbyl group having 3 to 30 carbon atoms and having at least one saturated ring composed of 3 to 30 carbon atoms,
divalent hydrocarbyl group having 6 to 30 carbon atoms, of which at least 6 carbon atoms are present in an aromatic system and the other carbon atoms, if present, are saturated,
a bridging radical having a chemical structure selected from the group consisting of (xix), (xx) with

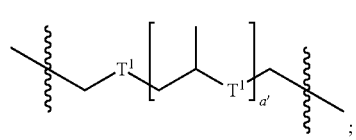
(xix)

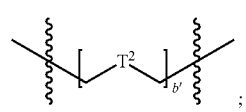
(xx)

where
T¹, T² are each independently selected from the group consisting of —O—, —S— and —NR''''— with R''''=unbranched or branched alkyl group having 1 to 6 carbon atoms,
where a' and b' are each independently an integer selected from the range of 1 to 50;
and where the $R^{24}$, $R^{25}$, $R^{26}$, $R^{27}$, $R^{28}$, $R^{29}$ radicals are selected from the group consisting of
hydrogen,
unbranched or branched alkyl group which has 1 to 30 carbon atoms and in which at least one hydrogen radical may be replaced by a radical selected from the group consisting of —OH, —OCH₃, —OCH₂CH₃, —N(CH₃)₂, —N(CH₂CH₃)₂, —N(CH₃)(CH₂CH₃),
unbranched or branched alkoxy group which has 1 to 30 carbon atoms and in which at least one hydrogen radical may be replaced by a radical selected from the group consisting of —OH, —OCH₃, —OCH₂CH₃, —N(CH₃)₂, —N(CH₂CH₃)₂, —N(CH₃)(CH₂CH₃),
a radical having a chemical structure selected from the group consisting of (xxi), (xxii), (xxiii), (xxiv), (xxv), (xxvi) with

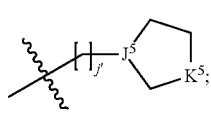
(xxi)

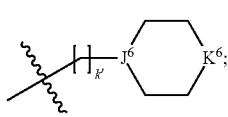
(xxii)

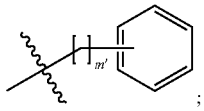
(xxiii)

-continued

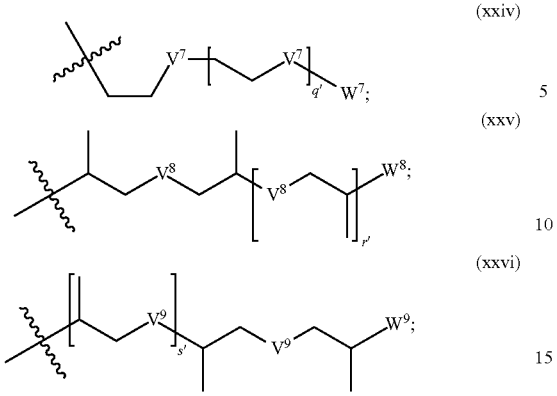

where J⁵, J⁶ are each independently selected from the group consisting of CH, N, where K⁵, K⁶ are each independently selected from the group consisting of —O—, N(CH₃)—, —N(CH₂CH₃)—, —S—, —CH₂—, where V⁷, V⁸, V⁹ are each independently selected from the group consisting of —O—, —S—, —NR''''— with R''''=unbranched or branched alkyl group having 1 to 6 carbon atoms, where W⁷, W⁸, W⁹ are each independently selected from the group consisting of H, methyl, ethyl, where j', k', m', q', r', s' are each independently an integer selected from the range of 0 to 50, where, in the chemical structure (xxi), (xxii), (xxiii), (xxiv), (xxv), (xxvi), at least one hydrogen radical may be replaced by a radical selected from the group consisting of —OH, —OCH₃, —OCH₂CH₃, —N(CH₃)₂, —N(CH₂CH₃)₂, —N(CH₃)(CH₂CH₃);

and where R²⁴, R²⁵, R²⁶, R²⁷, R²⁸, R²⁹ are each selected independently, with the exclusion of: R²⁴=R²⁵=hydrogen.

1.2 Process according to Point 1.1, where $p^1=p^2=p^3=p^4=p^5=p^6=p^8=p^9=p^{10}=p^{11}=0$ and where $p^7$, $p^{12}$, $p^{13}$, $p^{14}$, $p^{15}$, $p^{16}$ are each independently 0 or 1.

1.3 Process according to Point 1.1 or 1.2, where Y¹, Y², Y³, Y⁴, Y⁵, Y⁶, Y⁷, Y⁸, Y⁹ are each independently selected from the group consisting of
unbranched or branched alkylene group having 1 to 30 carbon atoms,
divalent saturated hydrocarbyl group having 3 to 30 carbon atoms and having at least one saturated ring composed of 3 to 30 carbon atoms;
where, preferably, Y¹, Y², Y³, Y⁴, Y⁵, Y⁶, Y⁷, Y⁸, Y⁹ are each independently an unbranched or branched alkylene group having 1 to 12, more preferably having 1 to 6, carbon atoms.

1.4 Process according to one or more of Points 1.1 to 1.3, where the R¹, R², R³, R⁴, R⁵, R⁶, R⁷, R⁸, R⁹, R¹⁰, R¹¹ radicals are each independently selected from the group consisting of
hydrogen,
unbranched or branched alkyl group which has 1 to 30 carbon atoms and in which at least one hydrogen radical may be replaced by a radical selected from the group consisting of —OH, —NH₂, —OCH₃, —OCH₂CH₃, —NH(CH₃), —N(CH₃)₂, —NH (CH₂CH₃), —N(CH₂CH₃)₂, —N(CH₃)(CH₂CH₃), a radical having a chemical structure (ix) with

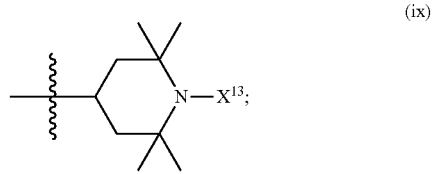

where X¹³ is selected from the group consisting of hydrogen, —OH, —O., unbranched or branched alkyl group having 1 to 10 carbon atoms, unbranched or branched alkoxy group having 1 to 10 carbon atoms;

and where the R¹², R¹³, R¹⁴, R¹⁵, R¹⁶, R¹⁷ radicals are each independently selected from the group consisting of
hydrogen,
unbranched or branched alkyl group having 1 to 30 carbon atoms,
a group having the chemical structure (x) with

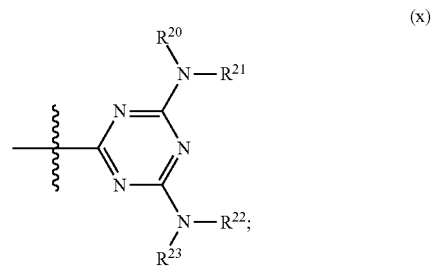

where the R¹⁸, R¹⁹, R²⁰, R²¹, R²², R²³ radicals are each independently selected from the group consisting of
hydrogen,
unbranched or branched alkyl group which has 1 to 30 carbon atoms and in which at least one hydrogen radical may be replaced by a radical selected from the group consisting of —OH, —NH₂, —OCH₃, —OCH₂CH₃, —NH(CH₃), —N(CH₃)₂, —NH (CH₂CH₃), —N(CH₂CH₃)₂, —N(CH₃)(CH₂CH₃), a radical having a chemical structure (xvii) with

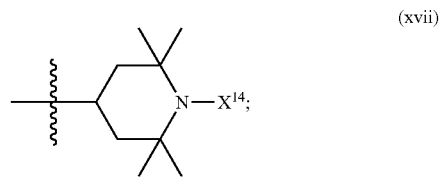

where X¹⁴ is selected from the group consisting of hydrogen, —OH, —O., unbranched or branched alkyl group having 1 to 10 carbon atoms, unbranched or branched alkoxy group having 1 to 10 carbon atoms, and with the proviso that R¹² and R¹⁷, when $p^{13}=p^{14}=p^{15}=p^{16}=0$, may each independently also be a group of the chemical structure (xviii) with

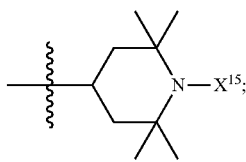

(xviii)

where X¹⁵ is selected from the group consisting of hydrogen, OH, —O., unbranched or branched alkyl group having 1 to 10 carbon atoms, unbranched or branched alkoxy group having 1 to 10 carbon atoms.

1.5 Process according to one or more of Points 1.1 to 1.4, where $X^1=X^2=X^3=X^4=X^5=X^6=X^7=X^8=X^9=X^{10}=X^{11}=X^{12}=X^{13}=X^{14}=X^{15}$=hydrogen.

1.6 Process according to one or more of Points 1.1 to 1.5, where the triacetonediamine compound (I) is selected from the group consisting of the chemical structures (I-A), (I-B) and where the $R^1$, $R^2$ radicals are each independently selected from the group consisting of
hydrogen,
unbranched or branched alkyl group which has 1 to 12 carbon atoms and in which at least one hydrogen radical may be replaced by a radical selected from the group consisting of —OH, —NH₂, —OCH₃, —OCH₂CH₃, —NH(CH₃), —N(CH₃)₂, —NH(CH₂CH₃), —N(CH₂CH₃)₂, —N(CH₃)(CH₂CH₃).

1.7 Process according to one or more of Points 1.1 to 1.6, where the triacetonediamine compound (I) is selected from the group consisting of the chemical structures (I-A), (I-B) and where the $R^1$, $R^2$ radicals are each independently selected from the group consisting of
hydrogen,
unbranched or branched alkyl group having 1 to 12 carbon atoms.

1.8 Process according to one or more of Points 1.1 to 1.7, where
$Z^1$, $Z^2$, $Z^3$ are each independently selected from the group consisting of direct bond,
unbranched or branched alkylene group having 1 to 30 carbon atoms,
divalent saturated hydrocarbyl group having 3 to 30 carbon atoms and having at least one saturated ring composed of 3 to 30 carbon atoms;
where, preferably, $Z^1$, $Z^2$, $Z^3$ are each independently an unbranched or branched alkylene group having 1 to 12 carbon atoms.

1.9 Process according to one or more of Points 1.1 to 1.8, where the carbonyl compound (II) is selected from the group consisting of the chemical structures (II-A), (II-B).

1.10 Process according to one or more of Points 1.1 to 1.9, where the triacetonediamine compound (I) is selected from the group consisting of the chemical structures (I-A), (I-B) and where the carbonyl compound (II) is selected from the group consisting of the chemical structures (II-A), (II-B), where
$p^1=p^2=0$;
$X^1=X^2=X^3$=hydrogen;
$Y^1$ and $Z^1$ are each independently an unbranched or branched alkylene group having 1 to 12, preferably 1 to 6, carbon atoms;
$R^1$, $R^2$ are each independently selected from the group consisting of
hydrogen,
unbranched or branched alkyl group having 1 to 12 carbon atoms;
$R^{24}$, $R^{25}$, $R^{26}$, $R^{27}$ are selected from the group consisting of
hydrogen,
unbranched or branched alkyl group having 1 to 12 carbon atoms;
where $R^{24}$, $R^{25}$, $R^{26}$, $R^{27}$ are each selected independently, with the exclusion of: $R^{24}=R^{25}$=hydrogen.

1.11 Process according to one or more of Points 1.1 to 1.10, where the triacetonediamine compound (I) has the chemical structure (I-A) and where the carbonyl compound (II) has the chemical structure (II-A), where
$X^1$=hydrogen;
$R^1$ is selected from the group consisting of
hydrogen,
unbranched or branched alkyl group having 1 to 8 and preferably 1 to 6 carbon atoms;
$R^{24}$, $R^{25}$ are selected from the group consisting of
hydrogen,
unbranched or branched alkyl group having 1 to 8 and preferably 1 to 6 carbon atoms;
where $R^{24}$, $R^{25}$ are each selected independently, with the exclusion of: $R^{24}=R^{25}$=hydrogen.

1.12 Process according to one or more of Points 1.1 to 1.11, where the triacetonediamine compound (I) has the chemical structure (I-A) and where the carbonyl compound (II) has the chemical structure (II-A), where $X^1$=H; $R^1$=H; $R^{24}$ is selected from the group consisting of hydrogen, methyl; $R^{25}$ is an unbranched or branched alkyl group having 1 to 8 carbon atoms.

1.13 Process according to one or more of Points 1.1 to 1.12, wherein reductive conditions are established by reacting the at least one triacetonediamine compound (I) with the at least one carbonyl compound (II) in the presence of hydrogen and in the presence of a supported catalyst, where the supported catalyst includes at least one metal M, where the metal M is selected from the group consisting of V, Cr, Mo, Mn, Ni, Pd, Pt, Fe, Ru, Os, Co, Rh, Ir, Cu.

1.14 Process according to one or more of Points 1.1 to 1.13, which is conducted in at least one solvent, where the solvent is selected from the group consisting of aliphatic solvents, aromatic solvents, ethers, halogenated solvents, amides, thio compounds, carboxylic acids, alcohols, water.

1.15 Process according to one or more of Points 1.1 to 1.14, which is conducted at a temperature in the range from 20° C. to 350° C. and a pressure in the range from 2 bar to 500 bar.

The present invention relates, in a second aspect, to a process according to the following Points 2.1 to 2.21:

2.1 Process for preparing an N-substituted triacetonediamine compound,
characterized in that at least one triacetonediamine compound (I) is reacted with at least one carbonyl compound (II) under reductive conditions,
where the triacetonediamine compound (I) is selected from the group consisting of the chemical structures (I-A), (I-B), (I-C), (I-D), (I-E) with

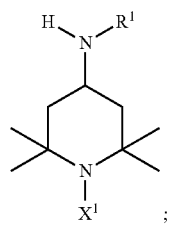 (I-A)

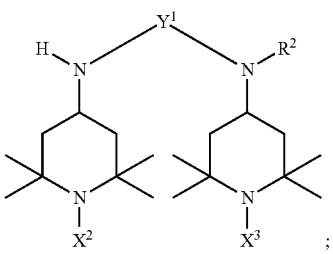 (I-B)

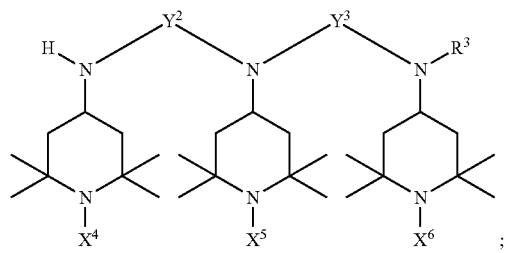 (I-C)

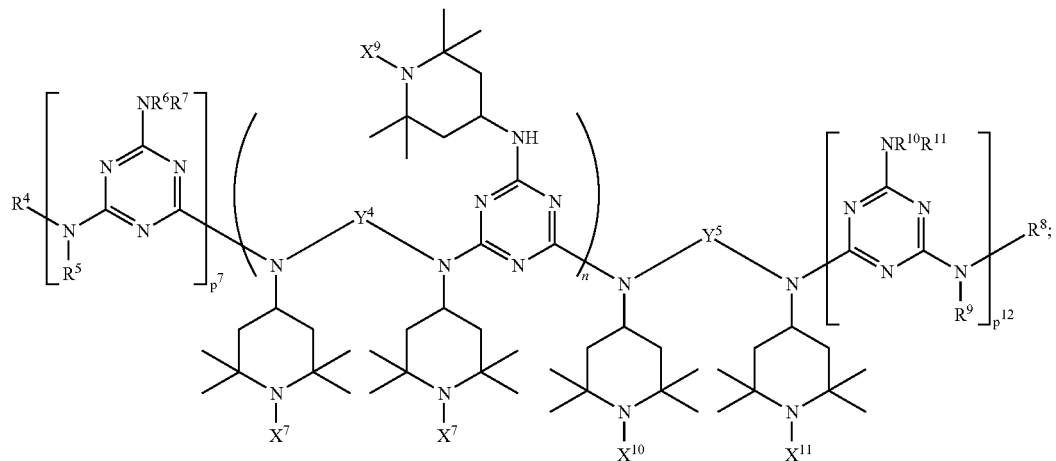 (I-D)

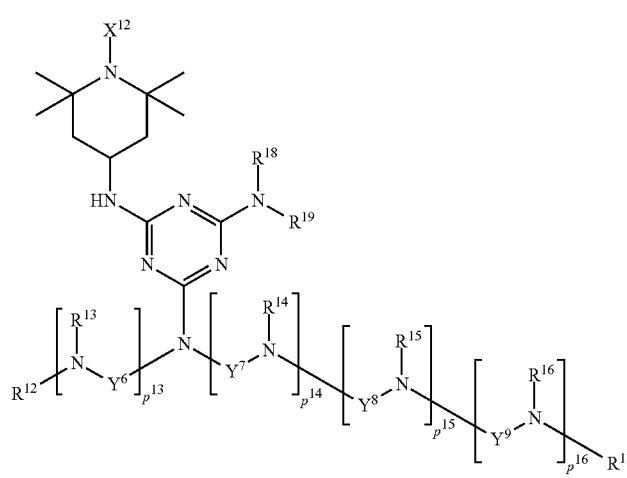 (I-E)

where n is an integer from the range of 1 to 20;

where $p^7, p^{12}, p^{13}, p^{14}, p^{15}, p^{16}$ are each independently 0 or 1;

where $X^1, X^2, X^3, X^4, X^5, X^6, X^7, X^8, X^9, X^{10}, X^{11}, X^{12}$ are each independently selected from the group consisting of hydrogen, OH, —O., unbranched or branched alkyl group having 1 to 10 carbon atoms, unbranched or branched alkoxy group having 1 to 10 carbon atoms;

where $Y^1, Y^2, Y^3, Y^4, Y^5, Y^6, Y^7, Y^8, Y^9$ are each independently selected from the group consisting of unbranched or branched alkylene group having 1 to 30 carbon atoms, divalent saturated hydrocarbyl group having 3 to 30 carbon atoms and having at least one saturated ring composed of 3 to 30 carbon atoms;

where the $R^1$, $R^2$, $R^3$, $R^4$, $R^5$, $R^6$, $R^7$, $R^8$, $R^9$, $R^{10}$, $R^{11}$ radicals are each independently selected from the group consisting of hydrogen, unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$), unbranched or branched acyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$), a radical having a chemical structure selected from the group consisting of (iii), (iv), (v), (vi), (vii), (viii), (ix) with

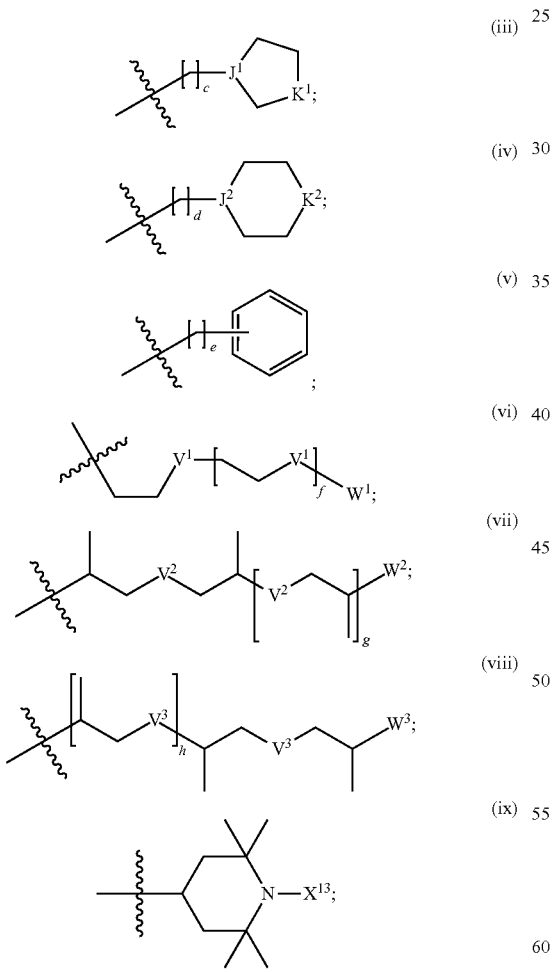

where $J^1$, $J^2$ are each independently selected from the group consisting of CH, N, where $K^1$, $K^2$ are each independently selected from the group consisting of —O—, —NH—, —N(CH$_3$)—, —N(CH$_2$CH$_3$)—, —S—, —CH$_2$—, where $V^1$, $V^2$, $V^3$ are each independently selected from the group consisting of —O—, —S—, —NH—, —NR"— with R"=unbranched or branched alkyl group having 1 to 6 carbon atoms, where $W^1$, $W^2$, $W^3$ are each independently selected from the group consisting of H, methyl, ethyl, where c, d, e, f, g, h are each independently an integer from the range of 0 to 50, where $X^{13}$ is selected from the group consisting of hydrogen, —OH, —O., unbranched or branched alkyl group having 1 to 10 carbon atoms, unbranched or branched alkoxy group having 1 to 10 carbon atoms, where, in the chemical structures (iii), (iv), (v), (vi), (vii), (viii), (ix), at least one hydrogen radical bonded to a carbon atom may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$);

where the $R^{12}$, $R^{13}$, $R^{14}$, $R^{15}$, $R^{16}$, $R^{17}$ radicals are each independently selected from the group consisting of hydrogen, unbranched or branched alkyl group having 1 to 30 carbon atoms, a group having the chemical structure (x) with

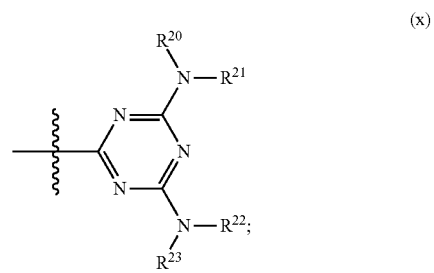

where the $R^{18}$, $R^{19}$, $R^{20}$, $R^{21}$, $R^{22}$, $R^{23}$ radicals are each independently selected from the group consisting of hydrogen, unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$), unbranched or branched acyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$), a radical having a chemical structure selected from the group consisting of (xi), (xii), (xiii), (xiv), (xv), (xvi), (xvii) with

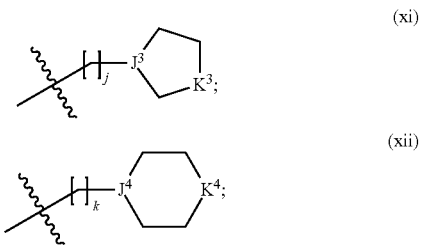

-continued

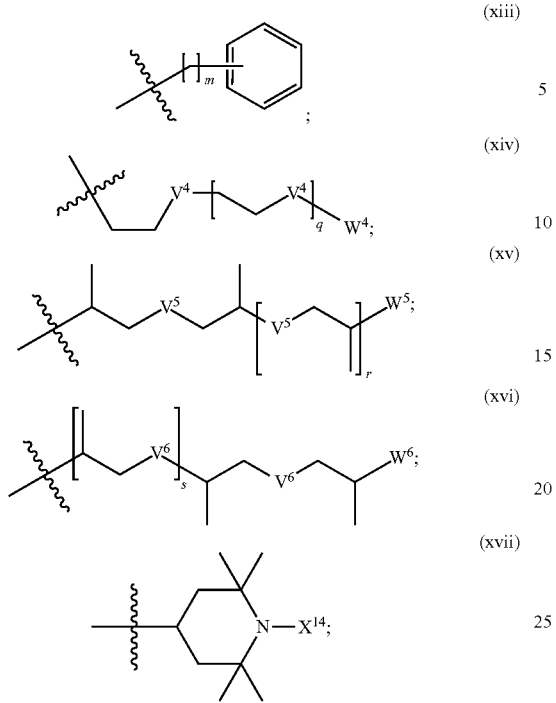

(xiii)

(xiv)

(xv)

(xvi)

(xvii)

where $J^3$, $J^4$ are each independently selected from the group consisting of CH, N,
where $K^3$, $K^4$ are each independently selected from the group consisting of —O—, —NH—, —N(CH$_3$)—, —N(CH$_2$CH$_3$)—, —S—, —CH$_2$—,
where $V^4$, $V^5$, $V^6$ are each independently selected from the group consisting of —O—, —S—, —NH—, —NR'''— with R'''=unbranched or branched alkyl group having 1 to 6 carbon atoms,
where $W^4$, $W^5$, $W^6$ are each independently selected from the group consisting of H, methyl, ethyl,
where j, k, m, q, r, s are each independently an integer from the range of 0 to 50,
where $X^{14}$ is selected from the group consisting of hydrogen, —OH, —O., unbranched or branched alkyl group having 1 to 10 carbon atoms, unbranched or branched alkoxy group having 1 to 10 carbon atoms,
where, in the chemical structures (xi), (xii), (xiii), (xiv), (xv), (xvi), (xvii), at least one hydrogen radical bonded to a carbon atom may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$),
and with the proviso that $R^{12}$ and $R^{17}$, when $p^{13}=p^{14}=p^{15}=p^{16}=0$, may each independently also be a group of the chemical structure (xviii) with

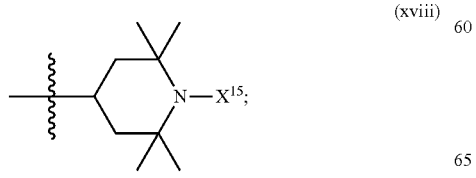

(xviii)

where $X^{15}$ is selected from the group consisting of hydrogen, OH, —O., unbranched or branched alkyl group having 1 to 10 carbon atoms, unbranched or branched alkoxy group having 1 to 10 carbon atoms;
and where the carbonyl compound (II) is selected from the group consisting of the chemical structures (II-A), (II-B), (II-C) with

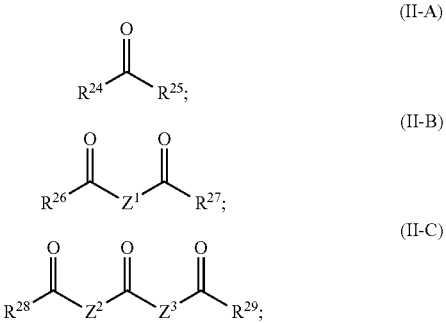

(II-A)

(II-B)

(II-C)

where $Z^1$, $Z^2$, $Z^3$ are each independently selected from the group consisting of direct bond,
  unbranched or branched alkylene group having 1 to 30 carbon atoms,
  divalent saturated hydrocarbyl group having 3 to 30 carbon atoms and having at least one saturated ring composed of 3 to 30 carbon atoms;
and where the $R^{24}$, $R^{25}$, $R^{26}$, $R^{27}$, $R^{28}$, $R^{29}$ radicals are selected from the group consisting of
hydrogen,
  unbranched or branched alkyl group which has 1 to 30 carbon atoms and in which at least one hydrogen radical may be replaced by a radical selected from the group consisting of —OH, —OCH$_3$, —OCH$_2$CH$_3$, —N(CH$_3$)$_2$, —N(CH$_2$CH$_3$)$_2$, —N(CH$_3$)(CH$_2$CH$_3$),
  unbranched or branched alkoxy group which has 1 to 30 carbon atoms and in which at least one hydrogen radical may be replaced by a radical selected from the group consisting of —OH, —OCH$_3$, —OCH$_2$CH$_3$, —N(CH$_3$)$_2$, —N(CH$_2$CH$_3$)$_2$, —N(CH$_3$)(CH$_2$CH$_3$),
  a radical having a chemical structure selected from the group consisting of (xxi), (xxii), (xxiv), (xxv), (xxvi) with

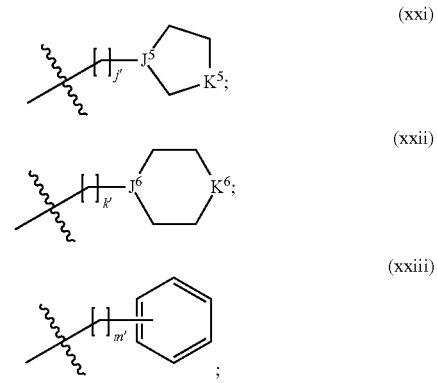

(xxi)

(xxii)

(xxiii)

-continued

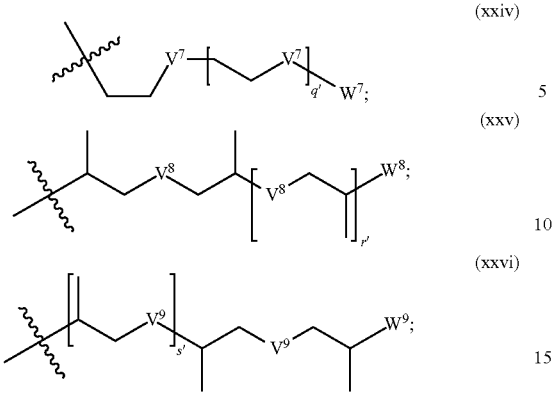

where J⁵, J⁶ are each independently selected from the group consisting of CH, N,
where K⁵, K⁶ are each independently selected from the group consisting of —O—, —N(CH₃)—, —N(CH₂CH₃)—, —S—, —CH₂—,
where V⁷, V⁸, V⁹ are each independently selected from the group consisting of —O—, —S—, —NR""— with R""=unbranched or branched alkyl group having 1 to 6 carbon atoms,
where W⁷, W⁸, W⁹ are each independently selected from the group consisting of H, methyl, ethyl,
where j', k', m', q', r', s' are each independently an integer selected from the range of 0 to 50,
where, in the chemical structure (xxi), (xxii), (xxiii), (xxiv), (xxv), (xxvi), at least one hydrogen radical may be replaced by a radical selected from the group consisting of —OH, —OCH₃, —OCH₂CH₃, —N(CH₃)₂, —N(CH₂CH₃)₂, —N(CH₃)(CH₂CH₃);
and where $R^{24}$, $R^{25}$, $R^{26}$, $R^{27}$, $R^{28}$, $R^{29}$ are each selected independently, with the exclusion of: $R^{24}=R^{25}$=hydrogen.

2.2 Process according to Point 2.1, where $Y^1$, $Y^2$, $Y^3$, $Y^4$, $Y^5$, $Y^6$, $Y^7$, $Y^8$, $Y^9$ are each independently selected from the group consisting of
unbranched or branched alkylene group having 1 to 12 carbon atoms,
divalent saturated hydrocarbyl group having 3 to 12 carbon atoms and having at least one saturated ring composed of 3 to 12 carbon atoms.

2.3 Process according to Point 2.1 or 2.2, where $Z^1$, $Z^2$, $Z^3$ are each independently selected from the group consisting of
direct bond,
unbranched or branched alkylene group having 1 to 12 carbon atoms,
divalent saturated hydrocarbyl group having 3 to 12 carbon atoms and having at least one saturated ring composed of 3 to 12 carbon atoms.

2.4 Process according to one or more of Points 2.1 to 2.3, where the $R^{24}$, $R^{25}$, $R^{26}$, $R^{27}$, $R^{28}$, $R^{29}$ radicals are selected from the group consisting of
hydrogen,
unbranched or branched alkyl group which has 1 to 30 carbon atoms and in which at least one hydrogen radical may be replaced by a radical selected from the group consisting of —OH, —OCH₃, —OCH₂CH₃, —N(CH₃)₂, —N(CH₂CH₃)₂, —N(CH₃)(CH₂CH₃);
and where $R^{24}$, $R^{25}$, $R^{26}$, $R^{27}$, $R^{28}$, $R^{29}$ are each selected independently, with the exclusion of: $R^{24}=R^{25}$=hydrogen.

2.5 Process according to one or more of Points 2.1 to 2.4, where the $R^1$, $R^2$, $R^3$, $R^4$, $R^5$, $R^6$, $R^7$, $R^8$, $R^9$, $R^{10}$, $R^{11}$ radicals are each independently selected from the group consisting of
hydrogen,
unbranched or branched alkyl group which has 1 to 12 carbon atoms and in which at least one hydrogen radical may be replaced by a radical selected from the group consisting of —OH, —NH₂, —OCH₃, —OCH₂CH₃, —NH(CH₃), —N(CH₃)₂, —NH(CH₂CH₃), —N(CH₂CH₃)₂, —N(CH₃)(CH₂CH₃),
a radical having a chemical structure (ix) with

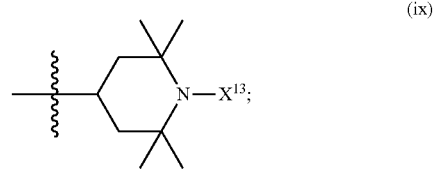

where $X^{13}$ is selected from the group consisting of hydrogen, —OH, —O., unbranched or branched alkyl group having 1 to 10 carbon atoms, unbranched or branched alkoxy group having 1 to 10 carbon atoms;
and where the $R^{12}$, $R^{13}$, $R^{14}$, $R^{15}$, $R^{16}$, $R^{17}$ radicals are each independently selected from the group consisting of
hydrogen,
unbranched or branched alkyl group having 1 to 12 carbon atoms,
a group having the chemical structure (x) with

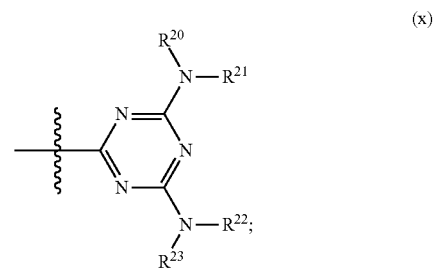

where the $R^{18}$, $R^{19}$, $R^{20}$, $R^{21}$, $R^{22}$, $R^{23}$ radicals are each independently selected from the group consisting of
hydrogen,
unbranched or branched alkyl group which has 1 to 12 carbon atoms and in which at least one hydrogen radical may be replaced by a radical selected from the group consisting of —OH, —NH₂, —OCH₃, —OCH₂CH₃, —NH(CH₃), —N(CH₃)₂, —NH(CH₂CH₃), —N(CH₂CH₃)₂, —N(CH₃)(CH₂CH₃),
a radical having a chemical structure (xvii) with

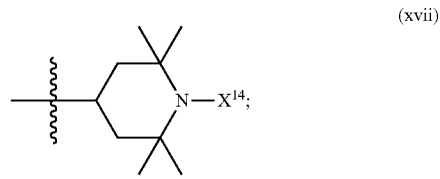

where $X^{14}$ is selected from the group consisting of hydrogen, —OH, —O., unbranched or branched alkyl group having 1 to 10 carbon atoms, unbranched or branched alkoxy group having 1 to 10 carbon atoms, and with the proviso that $R^{12}$ and $R^{17}$, when $p^{13}=p^{14}=p^{15}=p^{16}=0$, may each independently also be a group of the chemical structure (xviii) with

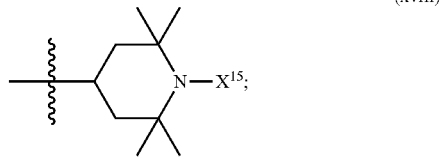

(xviii)

where $X^{15}$ is selected from the group consisting of hydrogen, OH, —O., unbranched or branched alkyl group having 1 to 10 carbon atoms, unbranched or branched alkoxy group having 1 to 10 carbon atoms.

2.6 Process according to one or more of Points 2.1 to 2.5, where the $R^{24}$, $R^{25}$, $R^{26}$, $R^{27}$, $R^{28}$, $R^{29}$ radicals are selected from the group consisting of
hydrogen,
unbranched or branched alkyl group which has 1 to 12 carbon atoms and in which at least one hydrogen radical may be replaced by a radical selected from the group consisting of —OH, —OCH$_3$, —OCH$_2$CH$_3$, —N(CH$_3$)$_2$, —N(CH$_2$CH$_3$)$_2$, —N(CH$_3$)(CH$_2$CH$_3$);
where $R^{24}$, $R^{25}$, $R^{26}$, $R^{27}$, $R^{28}$, $R^{29}$ are each selected independently, with the exclusion of: $R^{24}=R^{25}$=hydrogen.

2.7 Process according to one or more of Points 2.1 to 2.6, where $X^1=X^2=X^3=X^4=X^5=X^6=X^7=X^8=X^9=X^{10}=X^{11}=X^{12}=X^{13}=X^{14}=X^{15}$=hydrogen.

2.8 Process according to one or more of Points 2.1 to 2.7, where $Y^1$, $Y^2$, $Y^3$, $Y^4$, $Y^5$, $Y^6$, $Y^7$, $Y^8$, $Y^9$ are each independently selected from the group consisting of
unbranched or branched alkylene group having 1 to 6 carbon atoms,
divalent saturated hydrocarbyl group having 3 to 6 carbon atoms and having at least one saturated ring composed of 3 to 6 carbon atoms.

2.9 Process according to one or more of Points 2.1 to 2.8, where the triacetonediamine compound (I) is selected from the group consisting of the chemical structures (I-A), (I-B) and where the $R^1$, $R^2$ radicals are each independently selected from the group consisting of
hydrogen,
unbranched or branched alkyl group which has 1 to 12 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$).

2.10 Process according to Point 2.9, where the $R'$, $R^2$ radicals are each independently selected from the group consisting of
hydrogen,
unbranched or branched alkyl group having 1 to 12 carbon atoms.

2.11 Process according to Point 2.10, where the $R^1$, $R^2$ radicals are each independently selected from the group consisting of
hydrogen,
unbranched or branched alkyl group having 1 to 6 carbon atoms.

2.12 Process according to one or more of Points 2.1 to 2.11, where the carbonyl compound (II) has the chemical structure (II-A).

2.13 Process according to Point 2.12, where the $R^{24}$, $R^{25}$ radicals are selected from
hydrogen,
unbranched or branched alkyl group having 1 to 12 carbon atoms, and where $R^{24}$, $R^{25}$ are each selected independently, with the exclusion of: $R^{24}=R^{25}$=hydrogen.

2.14 Process according to Point 2.13, where the $R^{24}$, $R^{25}$ radicals are selected from
hydrogen,
unbranched or branched alkyl group having 1 to 6 carbon atoms,
and where $R^{24}$, $R^{25}$ are each selected independently, with the exclusion of: $R^{24}=R^{25}$=hydrogen.

2.15 Process according to one or more of Points 2.1 to 2.14, where the triacetonediamine compound (I) has the chemical structure (I-A)
and where the $R^1$ radical is selected from the group consisting of
hydrogen,
unbranched or branched alkyl group having 1 to 6 carbon atoms.

2.16 Process according to one or more of Points 2.1 to 2.15, where the $R^{24}$ radical is selected from the group consisting of hydrogen, methyl, ethyl and where the $R^{25}$ radical is selected from the group consisting of methyl, ethyl, n-propyl, iso-propyl, n-butyl, iso-butyl, sec-butyl, n-pentyl, n-hexyl, n-heptyl, n-octyl.

2.17 Process according to Point 2.16, where the $R^{24}$ radical is selected from the group consisting of hydrogen, methyl, and where the $R^{25}$ radical is selected from the group consisting of methyl, ethyl, n-propyl, iso-propyl, n-butyl, iso-butyl, sec-butyl, n-pentyl, n-hexyl, n-heptyl, n-octyl; where, even more preferably, the $R^{24}$ radical=hydrogen and the $R^{25}$ radical is selected from the group consisting of methyl, ethyl, n-propyl, iso-propyl, n-butyl, iso-butyl, sec-butyl, n-pentyl, n-hexyl, n-heptyl, n-octyl.

2.18 Process according to Point 2.16, where the $R^{24}$ radical=methyl, and where the $R^{25}$ radical is selected from the group consisting of methyl, ethyl, n-propyl, iso-propyl, n-butyl, iso-butyl, sec-butyl, n-pentyl, n-hexyl, n-heptyl, n-octyl.

2.19 Process according to one or more of Points 2.1 to 2.18, wherein reductive conditions are established by reacting the at least one triacetonediamine compound (I) with the at least one carbonyl compound (II) in the presence of hydrogen and in the presence of a supported catalyst, where the supported catalyst includes at least one metal M, where the metal M is selected from the group consisting of V, Cr, Mo, Mn, Ni, Pd, Pt, Fe, Ru, Os, Co, Rh, Ir, Cu.

2.20 Process according to one or more of Points 2.1 to 2.19, which is conducted in at least one solvent, where the solvent is selected from the group consisting of aliphatic solvents, aromatic solvents, ethers, halogenated solvents, amides, thio compounds, carboxylic acids, alcohols, water.

2.21 Process according to one or more of Points 2.1 to 2.20, which is conducted at a temperature in the range from 20° C. to 350° C. and a pressure in the range from 2 bar to 500 bar.

The present invention relates, in a third aspect, to a process according to the following Points 3.1 to 3.20:

3.1 Process for preparing an N-substituted triacetonediamine compound,
characterized in that at least one triacetonediamine compound (I) is reacted with at least one carbonyl compound (II) under reductive conditions, where the triacetonediamine compound (I) has the chemical structure (I-A) with

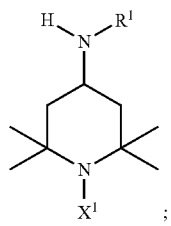
(I-A)

where X¹ is selected from the group consisting of hydrogen, OH, —O., unbranched or branched alkyl group having 1 to 10 carbon atoms, unbranched or branched alkoxy group having 1 to 10 carbon atoms;

where the R¹ radical is selected from the group consisting of
  hydrogen,
  unbranched or branched alkyl group which has 1 to 30 carbon atoms and in which at least one hydrogen radical may be replaced by a radical selected from the group consisting of —OH, —NH₂, —OCH₃, —OCH₂CH₃, —NH(CH₃), —N(CH₃)₂, —NH(CH₂CH₃), —N(CH₂CH₃)₂, —N(CH₃)(CH₂CH₃),
  unbranched or branched acyl group which has 1 to 30 carbon atoms and in which at least one hydrogen radical may be replaced by a radical selected from the group consisting of —OH, —NH₂, —OCH₃, —OCH₂CH₃, —NH(CH₃), —N(CH₃)₂, —NH(CH₂CH₃), —N(CH₂CH₃)₂, —N(CH₃)(CH₂CH₃),
  a radical having a chemical structure selected from the group consisting of (iii), (iv), (v), (vi), (vii), (viii), (ix) with

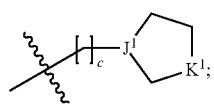
(iii)

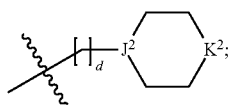
(iv)

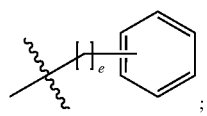
(v)

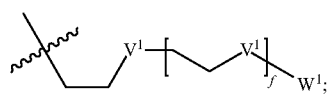
(vi)

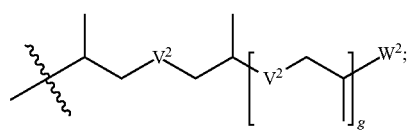
(vii)

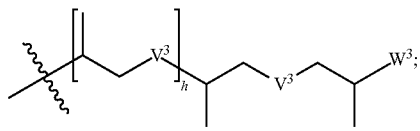
(viii)

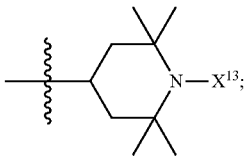
(ix)

where J¹, J² are each independently selected from the group consisting of CH, N, where K¹, K² are each independently selected from the group consisting of —O—, —NH—, —N(CH₃)—, —N(CH₂CH₃)—, —S—, —CH₂—, where V¹, V², V³ are each independently selected from the group consisting of —O—, —S—, —NH—, —NR"— with R"=unbranched or branched alkyl group having 1 to 6 carbon atoms, where W¹, W², W³ are each independently selected from the group consisting of H, methyl, ethyl, where c, d, e, f, g, h are each independently an integer from the range of 0 to 50, where X¹³ is selected from the group consisting of hydrogen, —OH, —O., unbranched or branched alkyl group having 1 to 10 carbon atoms, unbranched or branched alkoxy group having 1 to 10 carbon atoms, where, in the chemical structures (iii), (iv), (v), (vi), (vii), (viii), (ix), at least one hydrogen radical bonded to a carbon atom may be replaced by a radical selected from the group consisting of
  —OH, —NH₂, —OCH₃, —OCH₂CH₃, —NH(CH₃), —N(CH₃)₂, —NH(CH₂CH₃), —N(CH₂CH₃)₂, —N(CH₃)(CH₂CH₃);

and where the carbonyl compound (II) is selected from the group consisting of the chemical structures (II-A), (II-B) with

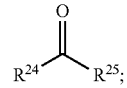
(II-A)

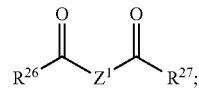
(II-B)

where Z¹ is selected from the group consisting of
  direct bond,
  unbranched or branched alkylene group having 1 to 30 carbon atoms,
  divalent saturated hydrocarbyl group having 3 to 30 carbon atoms and having at least one saturated ring composed of 3 to 30 carbon atoms,
  divalent hydrocarbyl group having 6 to 30 carbon atoms, of which at least 6 carbon atoms are present in an aromatic system and the other carbon atoms, if present, are saturated,
  a bridging radical having a chemical structure selected from the group consisting of (xix), (xx) with

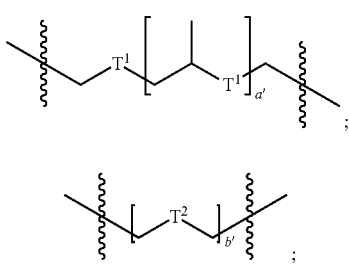

(xix)

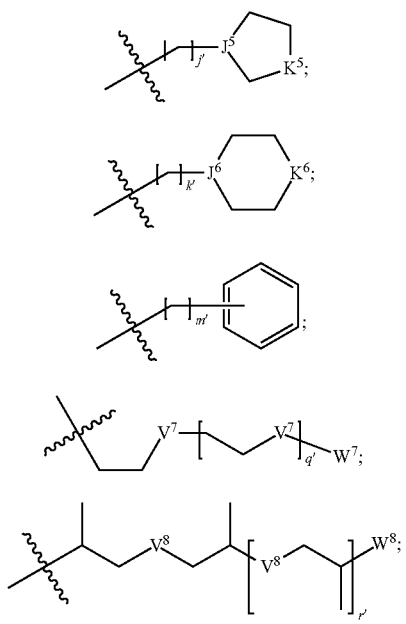

where

T¹, T² are each independently selected from the group consisting of —O—, —S— and —NR''''— with R''''=unbranched or branched alkyl group having 1 to 6 carbon atoms, where a' and b' are each independently an integer selected from the range of 1 to 50;

and where the $R^{24}$, $R^{25}$, $R^{26}$, $R^{27}$ radicals are selected from the group consisting of hydrogen, unbranched or branched alkyl group which has 1 to 30 carbon atoms and in which at least one hydrogen radical may be replaced by a radical selected from the group consisting of —OH, —OCH$_3$, —OCH$_2$CH$_3$, —N(CH$_3$)$_2$, —N(CH$_2$CH$_3$)$_2$, —N(CH$_3$)(CH$_2$CH$_3$), unbranched or branched alkoxy group which has 1 to 30 carbon atoms and in which at least one hydrogen radical may be replaced by a radical selected from the group consisting of —OH, —OCH$_3$, —OCH$_2$CH$_3$, —N(CH$_3$)$_2$, —N(CH$_2$CH$_3$)$_2$, —N(CH$_3$)(CH$_2$CH$_3$), a radical having a chemical structure selected from the group consisting of (xxi), (xxii), (xxiii), (xxiv), (xxv), (xxvi) with

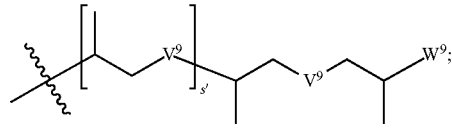

(xxvi)

where $J^5$, $J^6$ are each independently selected from the group consisting of CH, N, where $K^5$, $K^6$ are each independently selected from the group consisting of —O—, —N(CH$_3$)—, —N(CH$_2$CH$_3$)—, —S—, —CH$_2$—, where $V^7$, $V^8$, $V^9$ are each independently selected from the group consisting of —O—, —S—, —NR''''— with R''''=unbranched or branched alkyl group having 1 to 6 carbon atoms, where $W^7$, $W^8$, $W^9$ are each independently selected from the group consisting of H, methyl, ethyl, where j', k', m', q', r', s' are each independently an integer selected from the range of 0 to 50, where, in the chemical structure (xxi), (xxii), (xxiii), (xxiv), (xxv), (xxvi), at least one hydrogen radical may be replaced by a radical selected from the group consisting of —OH, —OCH$_3$, —OCH$_2$CH$_3$, —N(CH$_3$)$_2$, —N(CH$_2$CH$_3$)$_2$, —N(CH$_3$)(CH$_2$CH$_3$);

and where $R^{24}$, $R^{25}$, $R^{26}$, $R^{27}$ are each selected independently, with the exclusion of: $R^{24}=R^{25}$=hydrogen.

3.2 Process according to Point 3.1, where the $R^1$ radical is selected from the group consisting of hydrogen, unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$), a radical having a chemical structure (ix) with

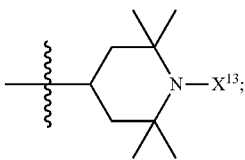

(ix)

3.3 Process according to Point 3.1 or 3.2, where $X^1=X^{13}$=hydrogen.

3.4 Process according to one or more of Points 3.1 to 3.3, where the $R^1$ radical is selected from the group consisting of hydrogen, unbranched or branched alkyl group which has 1 to 12 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$).

3.5 Process according to one or more of Points 3.1 to 3.4, where the $R^1$ radical is selected from the group consisting of hydrogen, unbranched or branched alkyl group having 1 to 12 carbon atoms.

3.6 Process according to one or more of Points 3.1 to 3.5, where $Z^1$ is selected from the group consisting of direct bond,
unbranched or branched alkylene group having 1 to 30 carbon atoms,
divalent saturated hydrocarbyl group having 3 to 30 carbon atoms and having at least one saturated ring composed of 3 to 30 carbon atoms.

3.7 Process according to Point 3.6, where $Z^1$ is selected from the group consisting of
direct bond,
unbranched or branched alkylene group having 1 to 12 and more preferably 1 to 6 carbon atoms.

3.8 Process according to one or more of Points 3.1 to 3.7, where the carbonyl compound (II) has the chemical structure (II-A).

3.9 Process according to Point 3.8, where
$X^1=X^{13}=$hydrogen;
$R^1$ is selected from the group consisting of
hydrogen,
unbranched or branched alkyl group having 1 to 12 carbon atoms;
and $R^{24}$, $R^{25}$ are selected from the group consisting of
hydrogen,
unbranched or branched alkyl group having 1 to 12 carbon atoms;
and where $R^{24}$, $R^{25}$ are each selected independently, with the exclusion of: $R^{24}=R^{25}=$hydrogen.

3.10 Process according to Point 3.9, where
$X^1=X^{13}=$hydrogen;
$R^1$ is selected from the group consisting of
hydrogen,
unbranched or branched alkyl group having 1 to 8 carbon atoms;
and $R^{24}$, $R^{25}$ are selected from the group consisting of
hydrogen,
unbranched or branched alkyl group having 1 to 8 carbon atoms;
and where $R^{24}$, $R^{25}$ are each selected independently, with the exclusion of: $R^{24}=R^{25}=$hydrogen.

3.11 Process according to Point 3.10, where
$X^1=X^{13}=$hydrogen;
$R^1=$hydrogen;
$R^{24}$ is selected from the group consisting of hydrogen, methyl;
$R^{25}=$unbranched or branched alkyl group having 1 to 8 carbon atoms.

3.12 Process according to one or more of Points 3.8 to 3.11, wherein 0.8 to 4.0, especially 0.9 to 3.0, preferably 1.2 to 2.6, more preferably 1.3 to 2.4, even more preferably 1.5 to 2.0 and most preferably 1.6 to 1.8 molar equivalents of the carbonyl compound (II) of the chemical structure (II-A) are used per triacetonediamine compound (I) of the chemical structure (I-A).

3.13 Process according to one or more of Points 3.8 to 3.12, wherein reductive conditions are established by reacting the at least one triacetonediamine compound (I) with the at least one carbonyl compound (II) in the presence of hydrogen and in the presence of a supported catalyst, where the supported catalyst includes at least one metal M, where the metal M is selected from the group consisting of V, Cr, Mo, Mn, Ni, Pd, Pt, Fe, Ru, Os, Co, Rh, Ir, Cu.

3.14 Process according to one or more of Points 3.8 to 3.13, which is conducted in at least one solvent, where the solvent is selected from the group consisting of aliphatic solvents, aromatic solvents, ethers, halogenated solvents, amides, thio compounds, carboxylic acids, alcohols, water.

3.15 Process according to one or more of Points 3.8 to 3.14, which is conducted at a temperature in the range from 20° C. to 350° C. and a pressure in the range from 2 bar to 500 bar.

3.16 Process according to one or more of Points 3.1 to 3.7, where the carbonyl compound (II) has the chemical structure (II-B).

3.17 Process according to Point 3.16, wherein 0.4 to 2.0, especially 0.45 to 1.5, preferably 0.6 to 1.3, more preferably 0.65 to 1.2, even more preferably 0.75 to 1.0 and most preferably 0.8 to 0.9 molar equivalents of the carbonyl compound (II) of the chemical structure (II-B) are used per triacetonediamine compound (I) of the chemical structure (I-A).

3.18 Process according to Point 3.16 or 3.17, wherein reductive conditions are established by reacting the at least one triacetonediamine compound (I) with the at least one carbonyl compound (II) in the presence of hydrogen and in the presence of a supported catalyst, where the supported catalyst includes at least one metal M, where the metal M is selected from the group consisting of V, Cr, Mo, Mn, Ni, Pd, Pt, Fe, Ru, Os, Co, Rh, Ir, Cu.

3.19 Process according to one or more of Points 3.16 to 3.18, which is conducted in at least one solvent, where the solvent is selected from the group consisting of aliphatic solvents, aromatic solvents, ethers, halogenated solvents, amides, thio compounds, carboxylic acids, alcohols, water.

3.20 Process according to one or more of Points 3.16 to 3.19, which is conducted at a temperature in the range from 20° C. to 350° C. and a pressure in the range from 2 bar to 500 bar.

The present invention relates, in a fourth aspect, to a process according to the following Points 4.1 to 4.22:

4.1 Process for preparing an N-substituted triacetonediamine compound,
characterized in that at least one triacetonediamine compound (I) is reacted with at least one carbonyl compound (II) under reductive conditions,
where the triacetonediamine compound (I) has the chemical structure (I-B) with

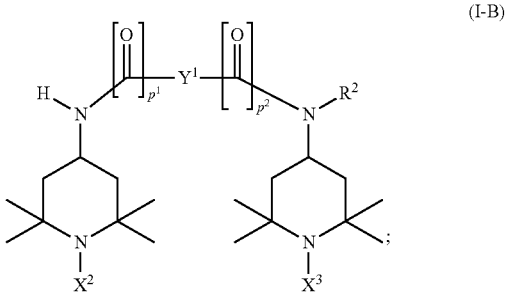

(I-B)

where $p^1$, $p^2$ are each independently 0 or 1;
where $X^2$, $X^3$ are each independently selected from the group consisting of hydrogen, OH, —O., unbranched or branched alkyl group having 1 to 10 carbon atoms, unbranched or branched alkoxy group having 1 to 10 carbon atoms;
where $Y^1$ is selected from the group consisting of
unbranched or branched alkylene group having 1 to 30 carbon atoms,
divalent saturated hydrocarbyl group having 3 to 30 carbon atoms and having at least one saturated ring composed of 3 to 30 carbon atoms, divalent hydrocarbyl group having 6 to 30 carbon atoms, of which at least 6 carbon atoms are present in an aromatic system and the other carbon atoms, if present, are saturated, a bridging radical having a chemical structure selected from the group consisting of (i), (ii) with

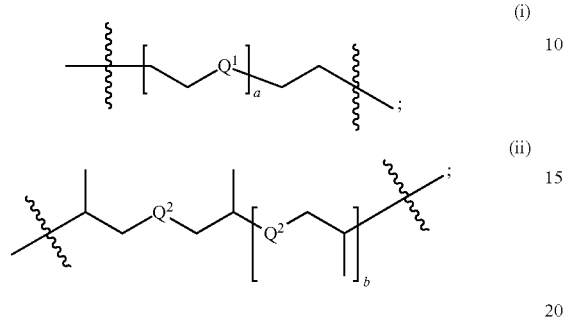

where
- $Q^1$, $Q^2$ are each independently selected from the group consisting of —O—, —S—, —NH— and —NR'— with R'=unbranched or branched alkyl group having 1 to 6 carbon atoms,
- where a is an integer selected from the range of 1 to 50,
- where b is an integer selected from the range of 0 to 50, and where $Y^1$ may also be a direct bond if at least one of $p^1$ and $p^2$ has the value of 1, where the $R^2$ radical is selected from the group consisting of
- hydrogen,
- unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$),
- unbranched or branched acyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$),
- a radical having a chemical structure selected from the group consisting of (iii), (iv), (v), (vi), (vii), (viii), (ix) with

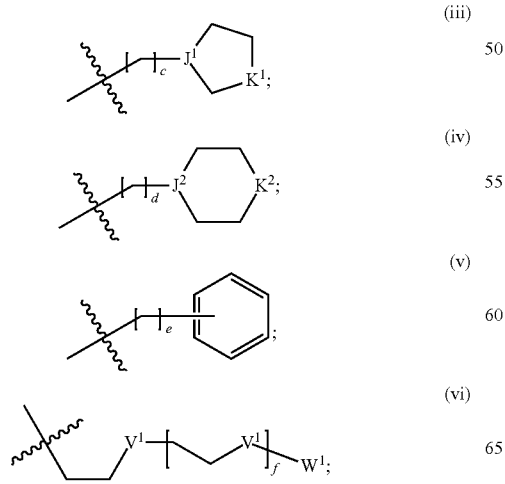

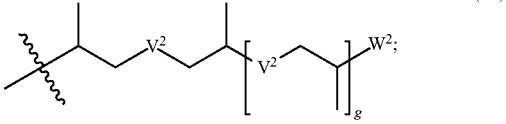

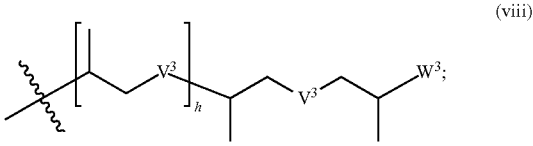

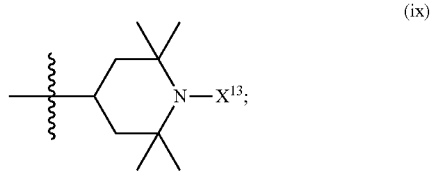

where $J^1$, $J^2$ are each independently selected from the group consisting of CH, N, where $K^1$, $K^2$ are each independently selected from the group consisting of —O—, —NH—, —N(CH$_3$)—, —N(CH$_2$CH$_3$)—, —S—, —CH$_2$—, where $V^1$, $V^2$, $V^3$ are each independently selected from the group consisting of —O—, —S—, —NH—, —NR"— with R"=unbranched or branched alkyl group having 1 to 6 carbon atoms, where $W^1$, $W^2$, $W^3$ are each independently selected from the group consisting of H, methyl, ethyl, where c, d, e, f, g, h are each independently an integer from the range of 0 to 50, where $X^{13}$ is selected from the group consisting of hydrogen, —OH, —O., unbranched or branched alkyl group having 1 to 10 carbon atoms, unbranched or branched alkoxy group having 1 to 10 carbon atoms, where, in the chemical structures (iii), (iv), (v), (vi), (vii), (viii), (ix), at least one hydrogen radical bonded to a carbon atom may be replaced by a radical selected from the group consisting of
—OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$);

and where the carbonyl compound (II) is selected from the group consisting of the chemical structures (II-A), (II-B) with

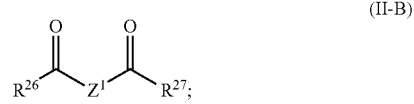

where $Z^1$ is selected from the group consisting of
- direct bond,
- unbranched or branched alkylene group having 1 to 30 carbon atoms,
- divalent saturated hydrocarbyl group having 3 to 30 carbon atoms and having at least one saturated ring composed of 3 to 30 carbon atoms, divalent hydrocarbyl group having 6 to 30 carbon atoms, of which at least 6 carbon atoms are present in an aromatic system and the other carbon atoms, if present, are saturated, a bridging radical having a chemical structure selected from the group consisting of (xix), (xx) with

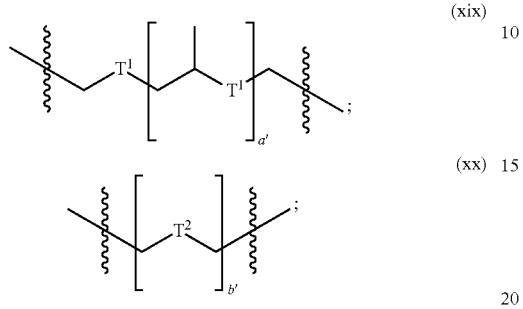

(xix)

(xx)

where
$T^1$, $T^2$ are each independently selected from the group consisting of —O—, —S— and —NR''''— with R''''=unbranched or branched alkyl group having 1 to 6 carbon atoms, where a' and b' are each independently an integer selected from the range of 1 to 50;

and where the $R^{24}$, $R^{25}$, $R^{26}$, $R^{27}$ radicals are selected from the group consisting of hydrogen, unbranched or branched alkyl group which has 1 to 30 carbon atoms and in which at least one hydrogen radical may be replaced by a radical selected from the group consisting of —OH, —OCH$_3$, —OCH$_2$CH$_3$, —N(CH$_3$)$_2$, —N(CH$_2$CH$_3$)$_2$, —N(CH$_3$)(CH$_2$CH$_3$), unbranched or branched alkoxy group which has 1 to 30 carbon atoms and in which at least one hydrogen radical may be replaced by a radical selected from the group consisting of —OH, —OCH$_3$, —OCH$_2$CH$_3$, —N(CH$_3$)$_2$, —N(CH$_2$CH$_3$)$_2$, —N(CH$_3$)(CH$_2$CH$_3$), a radical having a chemical structure selected from the group consisting of (xxi), (xxii), (xxiii), (xxiv), (xxv), (xxvi) with

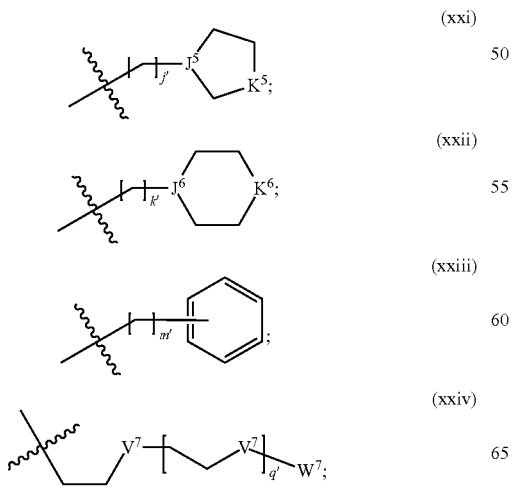

(xxi)

(xxii)

(xxiii)

(xxiv)

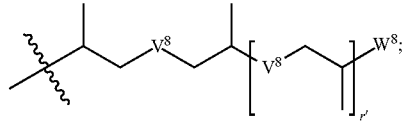

(xxv)

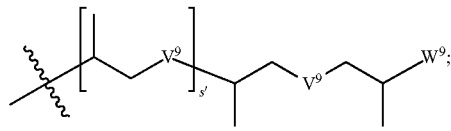

(xxvi)

where $J^5$, $J^6$ are each independently selected from the group consisting of CH, N, where $K^5$, $K^6$ are each independently selected from the group consisting of —O—, —N(CH$_3$)—, —N(CH$_2$CH$_3$)—, —S—, —CH$_2$—, where $V^7$, $V^8$, $V^9$ are each independently selected from the group consisting of —O—, —S—, —NR''''''— with R''''''=unbranched or branched alkyl group having 1 to 6 carbon atoms, where $W^7$, $W^8$, $W^9$ are each independently selected from the group consisting of H, methyl, ethyl, where j', k', m', q', r', s' are each independently an integer selected from the range of 0 to 50, where, in the chemical structure (xxi), (xxiii), (xxiv), (xxv), (xxvi), at least one hydrogen radical may be replaced by a radical selected from the group consisting of —OH, —OCH$_3$, —OCH$_2$CH$_3$, —N(CH$_3$)$_2$, —N(CH$_2$CH$_3$)$_2$, —N(CH$_3$)(CH$_2$CH$_3$);

and where $R^{24}$, $R^{25}$, $R^{26}$, $R^{27}$ are each selected independently, with the exclusion of: $R^{24}=R^{25}$=hydrogen.

4.2 Process according to Point 4.1, where $p^1=p^2=0$.

4.3 Process according to Point 4.1 or 4.2, where $Y^1$ is selected from the group consisting of unbranched or branched alkylene group having 1 to 30 carbon atoms, divalent saturated hydrocarbyl group having 3 to 30 carbon atoms and having at least one saturated ring composed of 3 to 30 carbon atoms;

where $Y^1$ is preferably an unbranched or branched alkylene group having 1 to 12 and more preferably having 1 to 6 carbon atoms.

4.4 Process according to one or more of Points 4.1 to 4.3, where the $R^2$ radical is selected from the group consisting of hydrogen, unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$), a radical having a chemical structure (ix) with

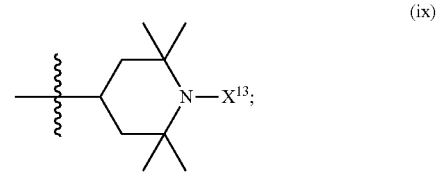

(ix)

where $X^{13}$ is selected from the group consisting of hydrogen, —OH, —O., unbranched or branched alkyl group having 1 to 10 carbon atoms, unbranched or branched alkoxy group having 1 to 10 carbon atoms.

4.5 Process according to one or more of Points 4.1 to 4.4, where $X^2=X^3=X^{13}=$hydrogen.

4.6 Process according to one or more of Points 4.1 to 4.5, where the $R^2$ radical is selected from the group consisting of
hydrogen,
unbranched or branched alkyl group which has 1 to 12 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$).

4.7 Process according to Point 4.6, where the $R^2$ radical is selected from the group consisting of
hydrogen,
unbranched or branched alkyl group having 1 to 12 carbon atoms.

4.8 Process according to one or more of Points 4.1 to 4.7, where $Z^1$ is selected from the group consisting of
direct bond,
unbranched or branched alkylene group having 1 to 30 carbon atoms,
divalent saturated hydrocarbyl group having 3 to 30 carbon atoms and having at least one saturated ring composed of 3 to 30 carbon atoms.

4.9 Process according to Point 4.8, where $Z^1$ is selected from the group consisting of
direct bond,
unbranched or branched alkylene group having 1 to 12 and more preferably 1 to 6 carbon atoms.

4.10 Process according to one or more of Points 4.1 to 4.9, where the carbonyl compound (II) has the chemical structure (II-A).

4.11 Process according to Point 4.10, where
$X^2=X^3=X^{13}=$hydrogen;
$R^2$ is selected from the group consisting of
hydrogen,
unbranched or branched alkyl group having 1 to 12 carbon atoms;
and $R^{24}$, $R^{25}$ are selected from the group consisting of
hydrogen,
unbranched or branched alkyl group having 1 to 12 carbon atoms;
and where $R^{24}$, $R^{25}$ are each selected independently, with the exclusion of: $R^{24}=R^{25}=$hydrogen.

4.12 Process according to Point 4.11, where
$X^2=X^3=X^{13}=$hydrogen;
$R^2$ is selected from the group consisting of
hydrogen,
unbranched or branched alkyl group having 1 to 8 carbon atoms;
and $R^{24}$, $R^{25}$ are selected from the group consisting of
hydrogen,
unbranched or branched alkyl group having 1 to 8 carbon atoms;
and where $R^{24}$, $R^{25}$ are each selected independently, with the exclusion of: $R^{24}=R^{25}=$hydrogen.

4.13 Process according to Point 4.12, where
$X^2=X^3=X^{13}=$hydrogen;
$R^2=$hydrogen;
and $R^{24}$ is selected from the group consisting of hydrogen, methyl;
$R^{25}$ is an unbranched or branched alkyl group having 1 to 8 carbon atoms.

4.14 Process according to one or more of Points 4.10 to 4.13, wherein 0.8 to 4.0, especially 0.9 to 3.0, preferably 1.2 to 2.6, more preferably 1.3 to 2.4, even more preferably 1.5 to 2.0 and most preferably 1.6 to 1.8 molar equivalents of the carbonyl compound (II) of the chemical structure (II-A) are used per triacetonediamine compound (I) of the chemical structure (I-A).

4.15 Process according to one or more of Points 4.10 to 4.14, wherein reductive conditions are established by reacting the at least one triacetonediamine compound (I) with the at least one carbonyl compound (II) in the presence of hydrogen and in the presence of a supported catalyst, where the supported catalyst includes at least one metal M, where the metal M is selected from the group consisting of V, Cr, Mo, Mn, Ni, Pd, Pt, Fe, Ru, Os, Co, Rh, Ir, Cu.

4.16 Process according to one or more of Points 4.10 to 4.15, which is conducted in at least one solvent, where the solvent is selected from the group consisting of aliphatic solvents, aromatic solvents, ethers, halogenated solvents, amides, thio compounds, carboxylic acids, alcohols, water.

4.17 Process according to one or more of Points 4.10 to 4.16, which is conducted at a temperature in the range from 20° C. to 350° C. and a pressure in the range from 2 bar to 500 bar.

4.18 Process according to one or more of Points 4.1 to 4.9, where the carbonyl compound (II) has the chemical structure (II-B).

4.19 Process according to Point 4.18, wherein 0.4 to 2.0, especially 0.45 to 1.5, preferably 0.6 to 1.3, more preferably 0.65 to 1.2, even more preferably 0.75 to 1.0 and most preferably 0.8 to 0.9 molar equivalents of the carbonyl compound (II) of the chemical structure (II-B) are used per triacetonediamine compound (I) of the chemical structure (I-A).

4.20 Process according to Point 4.18 or 4.19, wherein reductive conditions are established by reacting the at least one triacetonediamine compound (I) with the at least one carbonyl compound (II) in the presence of hydrogen and in the presence of a supported catalyst, where the supported catalyst includes at least one metal M, where the metal M is selected from the group consisting of V, Cr, Mo, Mn, Ni, Pd, Pt, Fe, Ru, Os, Co, Rh, Ir, Cu.

4.21 Process according to one or more of Points 4.18 to 4.20, which is conducted in at least one solvent, where the solvent is selected from the group consisting of aliphatic solvents, aromatic solvents, ethers, halogenated solvents, amides, thio compounds, carboxylic acids, alcohols, water.

4.22 Process according to one or more of Points 4.18 to 4.21, which is conducted at a temperature in the range from 20° C. to 350° C. and a pressure in the range from 2 bar to 500 bar.

The present invention relates, in a fifth aspect, to a process according to the following Points 5.1 to 5.16:

5.1 Process for preparing an N-substituted triacetonediamine compound,
characterized in that at least one triacetonediamine compound (I) is reacted with at least one carbonyl compound (II) under reductive conditions,
where the triacetonediamine compound (I) has the chemical structure (I-C) with

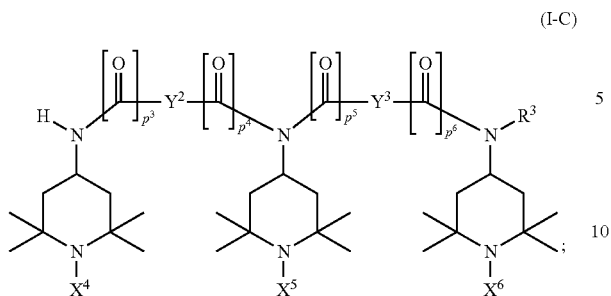
(I-C)

where $p^3$, $p^4$, $p^5$, $p^6$ are each independently 0 or 1;
where $X^4$, $X^5$, $X^6$ are each independently selected from the group consisting of hydrogen, OH, —O., unbranched or branched alkyl group having 1 to 10 carbon atoms, unbranched or branched alkoxy group having 1 to 10 carbon atoms;
where $Y^2$, $Y^3$ are each independently selected from the group consisting of
  unbranched or branched alkylene group having 1 to 30 carbon atoms,
  divalent saturated hydrocarbyl group having 3 to 30 carbon atoms and having at least one saturated ring composed of 3 to 30 carbon atoms,
  divalent hydrocarbyl group having 6 to 30 carbon atoms, of which at least 6 carbon atoms are present in an aromatic system and the other carbon atoms, if present, are saturated,
  a bridging radical having a chemical structure selected from the group consisting of (i), (ii) with

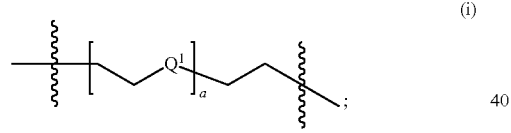
(i)

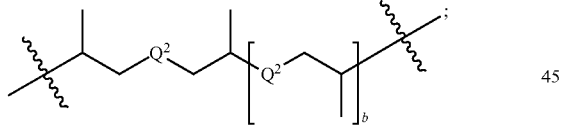
(ii)

where
  $Q^1$, $Q^2$ are each independently selected from the group consisting of —O—, —S—, —NH— and —NR'— with R'=unbranched or branched alkyl group having 1 to 6 carbon atoms,
  where a is an integer selected from the range of 1 to 50,
  where b is an integer selected from the range of 0 to 50,
and where $Y^2$ may also be a direct bond if at least one of $p^3$ and $p^4$ has the value of 1,
and where $Y^3$ may also be a direct bond if at least one of $p^5$ and $p^6$ has the value of 1,
where the $R^3$ radical is selected from the group consisting of
  hydrogen,
  unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$),
  unbranched or branched acyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$),
  a radical having a chemical structure selected from the group consisting of (iii), (iv), (v), (vi), (vii), (viii), (ix) with

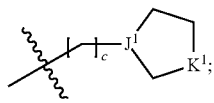
(iii)

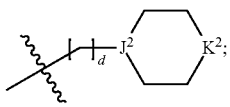
(iv)

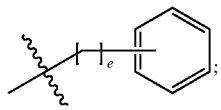
(v)

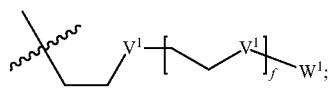
(vi)

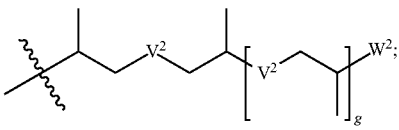
(vii)

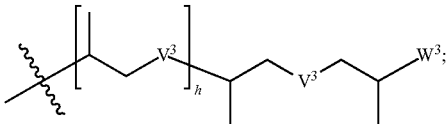
(viii)

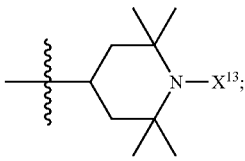
(ix)

where $J^1$, $J^2$ are each independently selected from the group consisting of CH, N,
where $K^1$, $K^2$ are each independently selected from the group consisting of —O—, —NH—, —N(CH$_3$)—, —N(CH$_2$CH$_3$)—, —S—, —CH$_2$—,
where $V^1$, $V^2$, $V^3$ are each independently selected from the group consisting of —O—, —S—, —NH—, —NR"— with R"=unbranched or branched alkyl group having 1 to 6 carbon atoms,
where $W^1$, $W^2$, $W^3$ are each independently selected from the group consisting of H, methyl, ethyl,
where c, d, e, f, g, h are each independently an integer from the range of 0 to 50,
where $X^{13}$ is selected from the group consisting of hydrogen, —OH, —O., unbranched or branched alkyl group having 1 to 10 carbon atoms, unbranched or branched alkoxy group having 1 to 10 carbon atoms, where, in the chemical structures (iii), (iv), (v), (vi), (vii), (viii), (ix), at least one hydrogen radical bonded to a carbon atom may be replaced by a radical selected from the group consisting of
—OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$);

and where the carbonyl compound (II) is selected from the group consisting of the chemical structures (II-A), (II-B) with

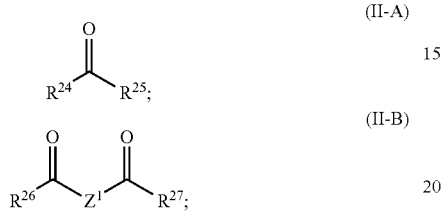

(II-A)

(II-B)

where Z$^1$ is selected from the group consisting of
direct bond,
unbranched or branched alkylene group having 1 to 30 carbon atoms,
divalent saturated hydrocarbyl group having 3 to 30 carbon atoms and having at least one saturated ring composed of 3 to 30 carbon atoms,
divalent hydrocarbyl group having 6 to 30 carbon atoms, of which at least 6 carbon atoms are present in an aromatic system and the other carbon atoms, if present, are saturated,
a bridging radical having a chemical structure selected from the group consisting of (xix), (xx) with

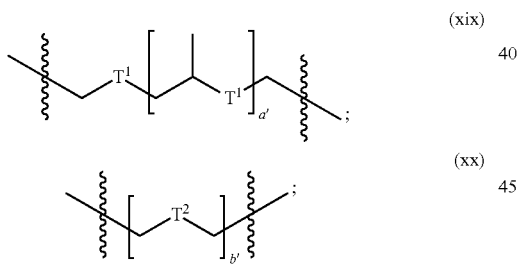

(xix)

(xx)

where
T$^1$, T$^2$ are each independently selected from the group consisting of —O—, —S— and —NR''''— with R''''=unbranched or branched alkyl group having 1 to 6 carbon atoms,
where a' and b' are each independently an integer selected from the range of 1 to 50;
and where the R$^{24}$, R$^{25}$, R$^{26}$, R$^{27}$ radicals are selected from the group consisting of
hydrogen,
unbranched or branched alkyl group which has 1 to 30 carbon atoms and in which at least one hydrogen radical may be replaced by a radical selected from the group consisting of —OH, —OCH$_3$, —OCH$_2$CH$_3$, —N(CH$_3$)$_2$, —N(CH$_2$CH$_3$)$_2$, —N(CH$_3$)(CH$_2$CH$_3$),
unbranched or branched alkoxy group which has 1 to 30 carbon atoms and in which at least one hydrogen radical may be replaced by a radical selected from the group consisting of —OH, —OCH$_3$, —OCH$_2$CH$_3$, —N(CH$_3$)$_2$, —N(CH$_2$CH$_3$)$_2$, —N(CH$_3$)(CH$_2$CH$_3$),
a radical having a chemical structure selected from the group consisting of (xxi), (xxii), (xxiii), (xxiv), (xxv), (xxvi) with

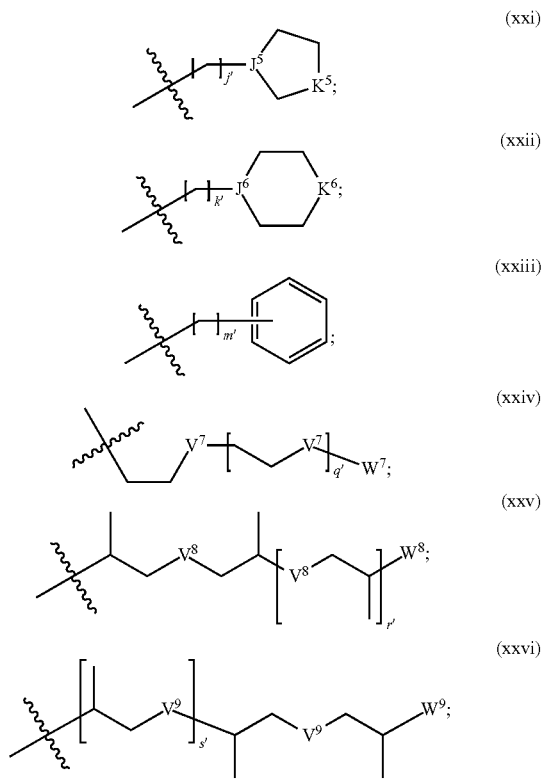

where J$^5$, J$^6$ are each independently selected from the group consisting of CH, N,
where K$^5$, K$^6$ are each independently selected from the group consisting of —O—, —N(CH$_3$)—, —N(CH$_2$CH$_3$)—, —S—,
where V$^7$, V$^8$, V$^9$ are each independently selected from the group consisting of —O—, —S—, —NR''''— with R''''=unbranched or branched alkyl group having 1 to 6 carbon atoms,
where W$^7$, W$^8$, W$^9$ are each independently selected from the group consisting of H, methyl, ethyl,
where j', k', m', q', r', s' are each independently an integer selected from the range of 0 to 50,
where, in the chemical structure (xxi), (xxii), (xxiii), (xxiv), (xxv), (xxvi), at least one hydrogen radical may be replaced by a radical selected from the group consisting of —OH, —OCH$_3$, —OCH$_2$CH$_3$, —N(CH$_3$)$_2$, —N(CH$_2$CH$_3$)$_2$, —N(CH$_3$)(CH$_2$CH$_3$);
and where R$^{24}$, R$^{25}$, R$^{26}$, R$^{27}$ are each selected independently, with the exclusion of: R$^{24}$=R$^{25}$=hydrogen.

5.2 Process according to Point 5.1, where p$^3$=p$^4$=p$^5$=p$^6$=0.

5.3 Process according to Point 5.1 or 5.2, where
Y$^2$, Y$^3$ are each independently selected from the group consisting of
unbranched or branched alkylene group having 1 to 30 carbon atoms,
divalent saturated hydrocarbyl group having 3 to 30 carbon atoms and having at least one saturated ring composed of 3 to 30 carbon atoms;

where, preferably, $Y^2$, $Y^3$ are each independently an unbranched or branched alkylene group having 1 to 12 and more preferably 1 to 6 carbon atoms.

5.4 Process according to one or more of Points 5.1 to 5.3, where the $R^3$ radical is selected from the group consisting of
hydrogen,
unbranched or branched alkyl group which has 1 to 30 carbon atoms and in which at least one hydrogen radical may be replaced by a radical selected from the group consisting of —OH, —$NH_2$, —$OCH_3$, —$OCH_2CH_3$, —$NH(CH_3)$, —$N(CH_3)_2$, —$NH(CH_2CH_3)$, —$N(CH_2CH_3)_2$, —$N(CH_3)(CH_2CH_3)$,
a radical having a chemical structure (ix) with

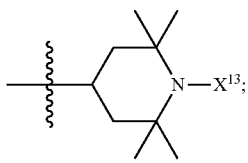

(ix)

where $X^{13}$ is selected from the group consisting of hydrogen, —OH, —O., unbranched or branched alkyl group having 1 to 10 carbon atoms, unbranched or branched alkoxy group having 1 to 10 carbon atoms.

5.5 Process according to one or more of Points 5.1 to 5.4, where $X^4=X^5=X^6$=hydrogen.

5.6 Process according to one or more of Points 5.1 to 5.5, where the $R^3$ radical is selected from the group consisting of
hydrogen,
unbranched or branched alkyl group which has 1 to 12 carbon atoms and in which at least one hydrogen radical may be replaced by a radical selected from the group consisting of —OH, —$NH_2$, —$OCH_3$, —$OCH_2CH_3$, —$NH(CH_3)$, —$N(CH_3)_2$, —$NH(CH_2CH_3)$, —$N(CH_2CH_3)_2$, —$N(CH_3)(CH_2CH_3)$.

5.7 Process according to one or more of Points 5.1 to 5.6, where the $R^3$ radical is selected from the group consisting of
hydrogen,
unbranched or branched alkyl group having 1 to 12 carbon atoms.

5.8 Process according to one or more of Points 5.1 to 5.7, where $Z^1$ is selected from the group consisting of
direct bond,
unbranched or branched alkylene group having 1 to 30 carbon atoms,
divalent saturated hydrocarbyl group having 3 to 30 carbon atoms and having at least one saturated ring composed of 3 to 30 carbon atoms.

5.9 Process according to Point 5.8, where $Z^1$ is selected from the group consisting of direct bond,
unbranched or branched alkylene group having 1 to 12 and preferably 1 to 6 carbon atoms.

5.10 Process according to one or more of Points 5.1 to 5.9, where the carbonyl compound (II) has the chemical structure (II-A).

5.11 Process according to Point 5.10, where $X^4=X^5=X^6=X^{13}$=hydrogen;
$R^3$ is selected from the group consisting of
hydrogen,
unbranched or branched alkyl group having 1 to 12 carbon atoms;
and $R^{24}$, $R^{25}$ are selected from the group consisting of
hydrogen,
unbranched or branched alkyl group having 1 to 12 carbon atoms;
and where $R^{24}$, $R^{25}$ are each selected independently, with the exclusion of: $R^{24}=R^{25}$=hydrogen.

5.12 Process according to Point 5.11, where $X^4=X^5=X^6=X^{13}$=hydrogen;
$R^3$ is selected from the group consisting of
hydrogen,
unbranched or branched alkyl group having 1 to 8 carbon atoms;
and $R^{24}$, $R^{25}$ are selected from the group consisting of
hydrogen,
unbranched or branched alkyl group having 1 to 8 carbon atoms;
and where $R^{24}$, $R^{25}$ are each selected independently, with the exclusion of: $R^{24}=R^{25}$=hydrogen.

5.13 Process according to Point 5.12, where $X^4=X^5=X^6=X^{13}$=hydrogen; $R^3$=hydrogen;
$R^{24}$ is selected from the group consisting of hydrogen, methyl;
$R^{25}$ is an unbranched or branched alkyl group having 1 to 8 carbon atoms.

5.14 Process according to one or more of Points 5.1 to 5.13, wherein reductive conditions are established by reacting the at least one triacetonediamine compound (I) with the at least one carbonyl compound (II) in the presence of hydrogen and in the presence of a supported catalyst, where the supported catalyst includes at least one metal M, where the metal M is selected from the group consisting of V, Cr, Mo, Mn, Ni, Pd, Pt, Fe, Ru, Os, Co, Rh, Ir, Cu.

5.15 Process according to one or more of Points 5.1 to 5.14, which is conducted in at least one solvent, where the solvent is selected from the group consisting of aliphatic solvents, aromatic solvents, ethers, halogenated solvents, amides, thio compounds, carboxylic acids, alcohols, water.

5.16 Process according to one or more of Points 5.1 to 5.15, which is conducted at a temperature in the range from 20° C. to 350° C. and a pressure in the range from 2 bar to 500 bar.

The present invention relates, in a sixth aspect, to a process according to the following Points 6.1 to 6.17:

6.1 Process for preparing an N-substituted triacetonediamine compound,
characterized in that at least one triacetonediamine compound (I) is reacted with at least one carbonyl compound (II) under reductive conditions,
where the triacetonediamine compound (I) has the chemical structure (I-D) with (I-D)

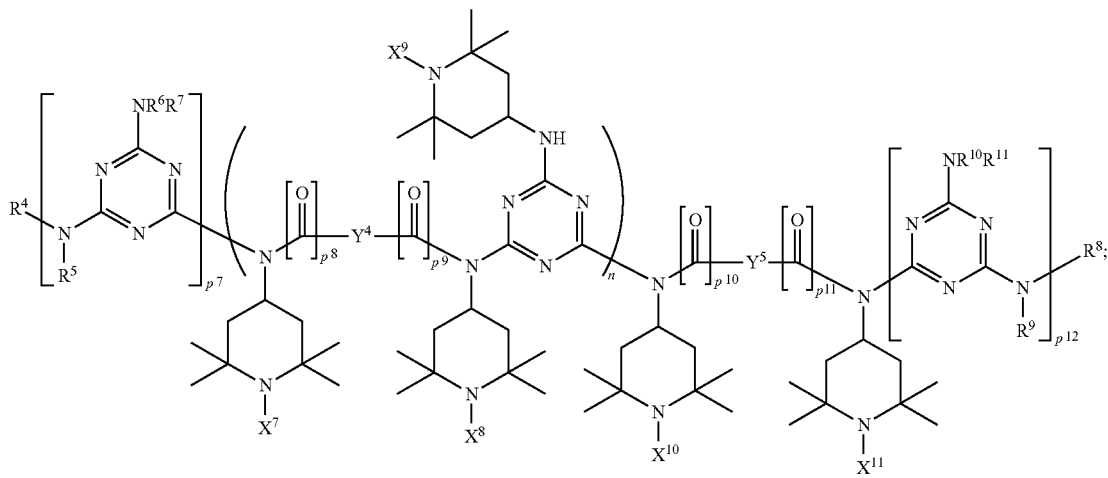

where n is an integer from the range of 1 to 20;
$p^8$, $p^9$, $p^{10}$, $p^{11}$, $p^{12}$ are each independently 0 or 1;
where $X^7$, $X^8$, $X^9$, $X^{10}$, $X^{11}$ are each independently selected from the group consisting of hydrogen, OH, —O., unbranched or branched alkyl group having 1 to 10 carbon atoms,
unbranched or branched alkoxy group having 1 to 10 carbon atoms;
where $Y^4$, $Y^5$ are each independently selected from the group consisting of
  unbranched or branched alkylene group having 1 to 30 carbon atoms,
  divalent saturated hydrocarbyl group having 3 to 30 carbon atoms and having at least one saturated ring composed of 3 to 30 carbon atoms,
  divalent hydrocarbyl group having 6 to 30 carbon atoms, of which at least 6 carbon atoms are present in an aromatic system and the other carbon atoms, if present, are saturated,
  a bridging radical having a chemical structure selected from the group consisting of (i), (ii) with

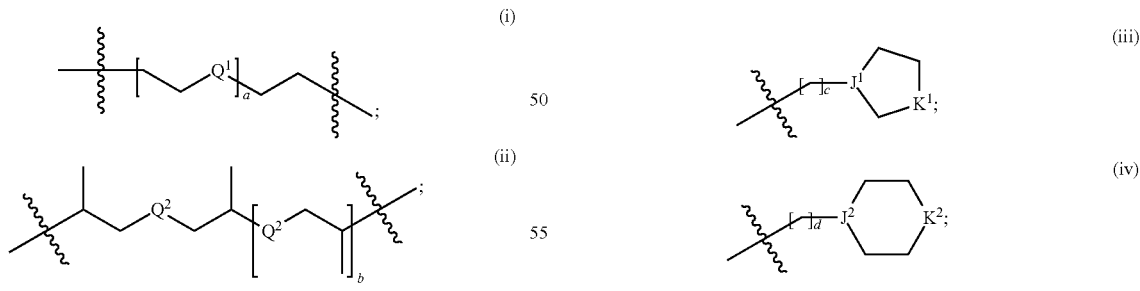

where
  $Q^1$, $Q^2$ are each independently selected from the group consisting of —O—, —S—, —NH— and —NR'— with R'=unbranched or branched alkyl group having 1 to 6 carbon atoms,
  where a is an integer selected from the range of 1 to 50,
  where b is an integer selected from the range of 0 to 50,
and where $Y^4$ may also be a direct bond if at least one of $p^8$ and $p^9$ has the value of 1, and where $Y^5$ may also be a direct bond if at least one of $p^{10}$ and $p^{11}$ has the value of 1;
where the $R^4$, $R^5$, $R^6$, $R^7$, $R^8$, $R^9$, $R^{10}$, $R^{11}$ radicals are each independently selected from the group consisting of
  hydrogen,
  unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$),
  unbranched or branched acyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$),
  a radical having a chemical structure selected from the group consisting of (iii), (iv), (v), (vi), (vii), (viii), (ix) with -continued

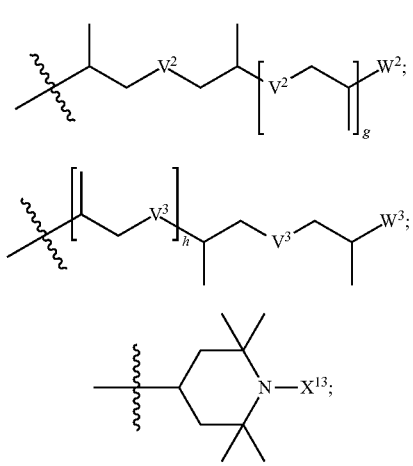

(vii)

(viii)

(ix)

where $J^1$, $J^2$ are each independently selected from the group consisting of CH, N, where $K^1$, $K^2$ are each independently selected from the group consisting of —O—, —NH—, —N(CH$_3$)—, —N(CH$_2$CH$_3$)—, —S—, —CH$_2$—, where $V^1$, $V^2$, $V^3$ are each independently selected from the group consisting of —O—, —S—, —NH—, —NR″— with R″=unbranched or branched alkyl group having 1 to 6 carbon atoms, where $W^1$, $W^2$, $W^3$ are each independently selected from the group consisting of H, methyl, ethyl, where c, d, e, f, g, h are each independently an integer from the range of 0 to 50, where $X^{13}$ is selected from the group consisting of hydrogen, —OH, —O., unbranched or branched alkyl group having 1 to 10 carbon atoms, unbranched or branched alkoxy group having 1 to 10 carbon atoms, where, in the chemical structures (iii), (iv), (v), (vi), (vii), (viii), (ix), at least one hydrogen radical bonded to a carbon atom may be replaced by a radical selected from the group consisting of
—OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$);

and where the carbonyl compound (II) is selected from the group consisting of the chemical structures (II-A), (II-B) with

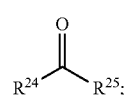

(II-A)

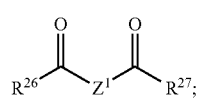

(II-B)

where $Z^1$ is selected from the group consisting of
  direct bond,
  unbranched or branched alkylene group having 1 to 30 carbon atoms,
  divalent saturated hydrocarbyl group having 3 to 30 carbon atoms and having at least one saturated ring composed of 3 to 30 carbon atoms,
  divalent hydrocarbyl group having 6 to 30 carbon atoms, of which at least 6 carbon atoms are present in an aromatic system and the other carbon atoms, if present, are saturated,
  a bridging radical having a chemical structure selected from the group consisting of (xix), (xx) with

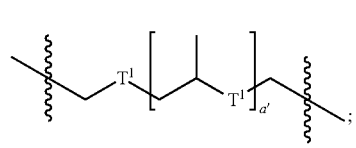

(xix)

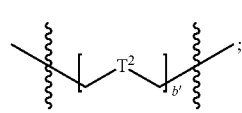

(xx)

where
  $T^1$, $T^2$ are each independently selected from the group consisting of —O—, —S— and —NR″″— with R″″=unbranched or branched alkyl group having 1 to 6 carbon atoms,
  where a' and b' are each independently an integer selected from the range of 1 to 50;

and where the $R^{24}$, $R^{25}$, $R^{26}$, $R^{27}$ radicals are selected from the group consisting of
  hydrogen,
  unbranched or branched alkyl group which has 1 to 30 carbon atoms and in which at least one hydrogen radical may be replaced by a radical selected from the group consisting of —OH, —OCH$_3$, —OCH$_2$CH$_3$, —N(CH$_3$)$_2$, —N(CH$_2$CH$_3$)$_2$, —N(CH$_3$)(CH$_2$CH$_3$),
  unbranched or branched alkoxy group which has 1 to 30 carbon atoms and in which at least one hydrogen radical may be replaced by a radical selected from the group consisting of —OH, —OCH$_3$, —OCH$_2$CH$_3$, —N(CH$_3$)$_2$, —N(CH$_2$CH$_3$)$_2$, —N(CH$_3$)(CH$_2$CH$_3$),
  a radical having a chemical structure selected from the group consisting of (xxi), (xxii), (xxiii), (xxiv), (xxv), (xxvi) with

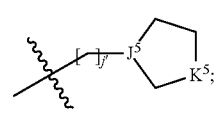

(xxi)

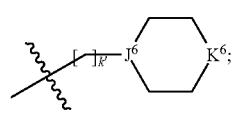

(xxii)

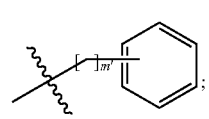

(xxiii)

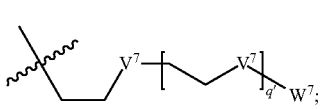

(xxiv)

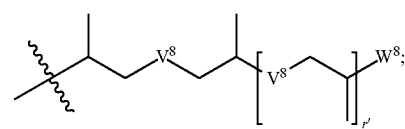

(xxv)

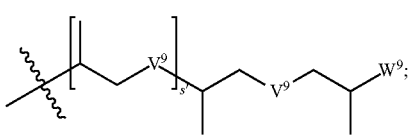

(xxvi)

where $J^5$, $J^6$ are each independently selected from the group consisting of CH, N,
where $K^5$, $K^6$ are each independently selected from the group consisting of —O—, —N(CH$_3$)—, —N(CH$_2$CH$_3$)—, —S—, —CH$_2$—,
where $V^7$, $V^8$, $V^9$ are each independently selected from the group consisting of —O—, —S—, —NR''''— with R''''=unbranched or branched alkyl group having 1 to 6 carbon atoms,
where $W^7$, $W^8$, $W^9$ are each independently selected from the group consisting of H, methyl, ethyl,
where j', k', m', q', r', s' are each independently an integer selected from the range of 0 to 50,
where, in the chemical structure (xxi), (xxii), (xxiii), (xxiv), (xxv), (xxvi), at least one hydrogen radical may be replaced by a radical selected from the group consisting of —OH, —OCH$_3$, —OCH$_2$CH$_3$, —N(CH$_3$)$_2$, —N(CH$_2$CH$_3$)$_2$, —N(CH$_3$)(CH$_2$CH$_3$);
and where $R^{24}$, $R^{25}$, $R^{26}$, $R^{27}$ are each selected independently, with the exclusion of: $R^{24}$=$R^{25}$=hydrogen.

6.2 Process according to Point 6.1, where $p^8$=$p^9$=$p^{10}$=$p^{11}$=0 and where $p^7$, $p^{12}$ are each independently 0 or 1.

6.3 Process according to Point 6.1 or 6.2, where $Y^4$, $Y^5$ are each independently selected from the group consisting of
unbranched or branched alkylene group having 1 to 30 carbon atoms,
divalent saturated hydrocarbyl group having 3 to 30 carbon atoms and having at least one saturated ring composed of 3 to 30 carbon atoms;
where, preferably, $Y^4$, $Y^5$ are each independently an unbranched or branched alkylene group having 1 to 12 and more preferably 1 to 6 carbon atoms.

6.4 Process according to one or more of Points 6.1 to 6.3, where the $R^4$, $R^5$, $R^6$, $R^7$, $R^8$, $R^9$, $R^{10}$, $R^{11}$ radicals are each independently selected from the group consisting of
hydrogen,
unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$),
a radical having a chemical structure (ix) with

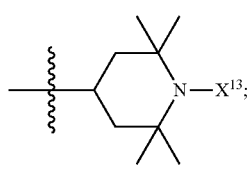

(ix)

where $X^{13}$ is selected from the group consisting of hydrogen, —OH, —O., unbranched or branched alkyl group having 1 to 10 carbon atoms, unbranched or branched alkoxy group having 1 to 10 carbon atoms.

6.5 Process according to one or more of Points 6.1 to 6.4, where $X^7$=$X^8$=$X^9$=$X^{10}$=$X^{11}$=$X^{13}$=hydrogen.

6.6 Process according to one or more of Points 6.1 to 6.5, where the $R^4$, $R^5$, $R^6$, $R^7$, $R^8$, $R^9$, $R^{10}$, $R^{11}$ radicals are each independently selected from the group consisting of
hydrogen,
unbranched or branched alkyl group which has 1 to 12 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$).

6.7 Process according to Point 6.6, where the $R^4$, $R^5$, $R^6$, $R^7$, $R^8$, $R^9$, $R^{10}$, $R^{11}$ radicals are each independently selected from the group consisting of
hydrogen,
unbranched or branched alkyl group having 1 to 12 carbon atoms.

6.8 Process according to one or more of Points 6.1 to 6.7, where $Z^1$ is selected from the group consisting of
direct bond,
unbranched or branched alkylene group having 1 to 30 carbon atoms,
divalent saturated hydrocarbyl group having 3 to 30 carbon atoms and having at least one saturated ring composed of 3 to 30 carbon atoms.

6.9 Process according to Point 6.8, where $Z^1$ is selected from the group consisting of
direct bond,
unbranched or branched alkylene group having 1 to 12 and preferably 1 to 6 carbon atoms.

6.10 Process according to one or more of Points 6.1 to 6.9, where the carbonyl compound (II) has the chemical structure (II-A).

6.11 Process according to Point 6.10, where
$X^7$=$X^8$=$X^9$=$X^{10}$=$X^{11}$=$X^{13}$=hydrogen;
$R^4$, $R^5$, $R^6$, $R^7$, $R^8$, $R^9$, $R^{10}$, $R^{11}$ are each independently selected from the group consisting of
hydrogen,
unbranched or branched alkyl group having 1 to 12 carbon atoms;
$R^{24}$, $R^{25}$ are selected from the group consisting of
hydrogen,
unbranched or branched alkyl group having 1 to 12 carbon atoms;
and where $R^{24}$, $R^{25}$ are each selected independently, with the exclusion of: $R^{24}$=$R^{25}$=hydrogen.

6.12 Process according to Point 6.11, where
$X^7$=$X^8$=$X^9$=$X^{10}$=$X^{11}$=$X^{13}$=hydrogen;
$R^4$, $R^5$, $R^6$, $R^7$, $R^8$, $R^9$, $R^{10}$, $R^{11}$ are each independently selected from the group consisting of
hydrogen,
unbranched or branched alkyl group having 1 to 8 carbon atoms;
$R^{24}$, $R^{25}$ are selected from the group consisting of
hydrogen,
unbranched or branched alkyl group having 1 to 8 carbon atoms;
and where $R^{24}$, $R^{25}$ are each selected independently, with the exclusion of: $R^{24}$=$R^{25}$=hydrogen.

6.13 Process according to Point 6.12, where
$X^7=X^8=X^9=X^{10}=X^{11}=X^{13}$=hydrogen;
$R^4$, $R^5$, $R^6$, $R^7$, $R^8$, $R^9$, $R^{10}$, $R^{11}$ are each independently selected from the group consisting of
  hydrogen,
  unbranched or branched alkyl group having 1 to 6 carbon atoms;
$R^{24}$ is selected from the group consisting of hydrogen, methyl;
$R^{25}$ is an unbranched or branched alkyl group having 1 to 8 carbon atoms.

6.14 Process according to Point 6.13, where
$X^7=X^8=X^9=X^{10}=X^{11}=X^{13}$=hydrogen;
$R^4$, $R^5$, $R^6$, $R^7$, $R^8$, $R^9$, $R^{10}$, $R^{11}$ are each independently an unbranched or branched alkyl group having 1 to 6 carbon atoms;
$R^{24}$ is selected from the group consisting of hydrogen, methyl;
$R^{25}$ is an unbranched or branched alkyl group having 1 to 8 carbon atoms.

6.15 Process according to one or more of Points 6.1 to 6.14, wherein reductive conditions are established by reacting the at least one triacetonediamine compound (I) with the at least one carbonyl compound (II) in the presence of hydrogen and in the presence of a supported catalyst, where the supported catalyst includes at least one metal M, where the metal M is selected from the group consisting of V, Cr, Mo, Mn, Ni, Pd, Pt, Fe, Ru, Os, Co, Rh, Ir, Cu.

6.16 Process according to one or more of Points 6.1 to 6.15, which is conducted in at least one solvent, where the solvent is selected from the group consisting of aliphatic solvents, aromatic solvents, ethers, halogenated solvents, amides, thio compounds, carboxylic acids, alcohols, water.

6.17 Process according to one or more of Points 6.1 to 6.16, which is conducted at a temperature in the range from 20° C. to 350° C. and a pressure in the range from 2 bar to 500 bar.

The present invention relates, in a seventh aspect, to a process according to the following Points 7.1 to 7.14:

7.1 Process for preparing an N-substituted triacetonediamine compound,
characterized in that at least one triacetonediamine compound (I) is reacted with at least one carbonyl compound (II) under reductive conditions,
  where the triacetonediamine compound (I) has the chemical structure (I-E) with

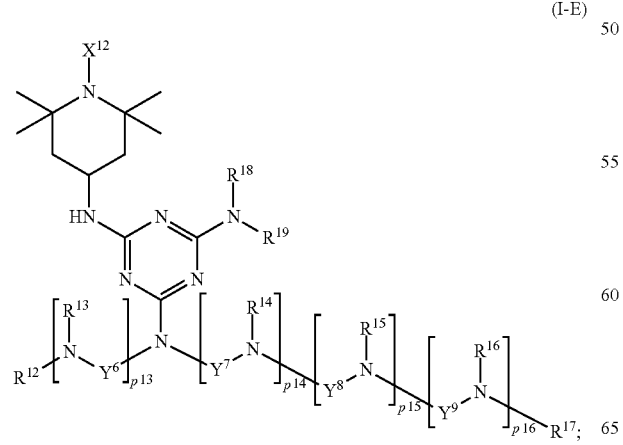

(I-E)

where $p^{13}$, $p^{14}$, $p^{15}$, $p^{16}$ are each independently 0 or 1;
where $X^{12}$ is selected from the group consisting of hydrogen, OH, —O., unbranched or branched alkyl group having 1 to 10 carbon atoms, unbranched or branched alkoxy group having 1 to 10 carbon atoms;
where $Y^6$, $Y^7$, $Y^8$, $Y^9$ are each independently selected from the group consisting of
  unbranched or branched alkylene group having 1 to 30 carbon atoms,
  divalent saturated hydrocarbyl group having 3 to 30 carbon atoms and having at least one saturated ring composed of 3 to 30 carbon atoms,
  divalent hydrocarbyl group having 6 to 30 carbon atoms, of which at least 6 carbon atoms are present in an aromatic system and the other carbon atoms, if present, are saturated,
  a bridging radical having a chemical structure selected from the group consisting of (i), (ii) with

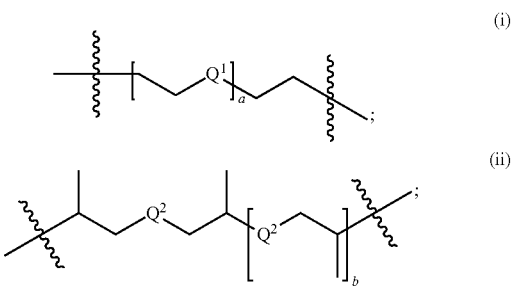

where
  $Q^1$, $Q^2$ are each independently selected from the group consisting of —O—, —S—, —NH— and —NR'— with R'=unbranched or branched alkyl group having 1 to 6 carbon atoms,
  where a is an integer selected from the range of 1 to 50,
  where b is an integer selected from the range of 0 to 50,
where the $R^{12}$, $R^{13}$, $R^{14}$, $R^{15}$, $R^{16}$, $R^{17}$ radicals are each independently selected from the group consisting of
  hydrogen,
  unbranched or branched alkyl group having 1 to 30 carbon atoms,
  a group having the chemical structure (x) with

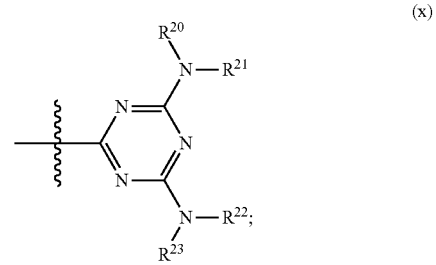

(x)

where the $R^{18}$, $R^{19}$, $R^{20}$, $R^{21}$, $R^{22}$, $R^{23}$ radicals are each independently selected from the group consisting of
  hydrogen,
  unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$),
unbranched or branched acyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$),
a radical having a chemical structure selected from the group consisting of (xi), (xii), (xiii), (xiv), (xv), (xvi), (xvii) with

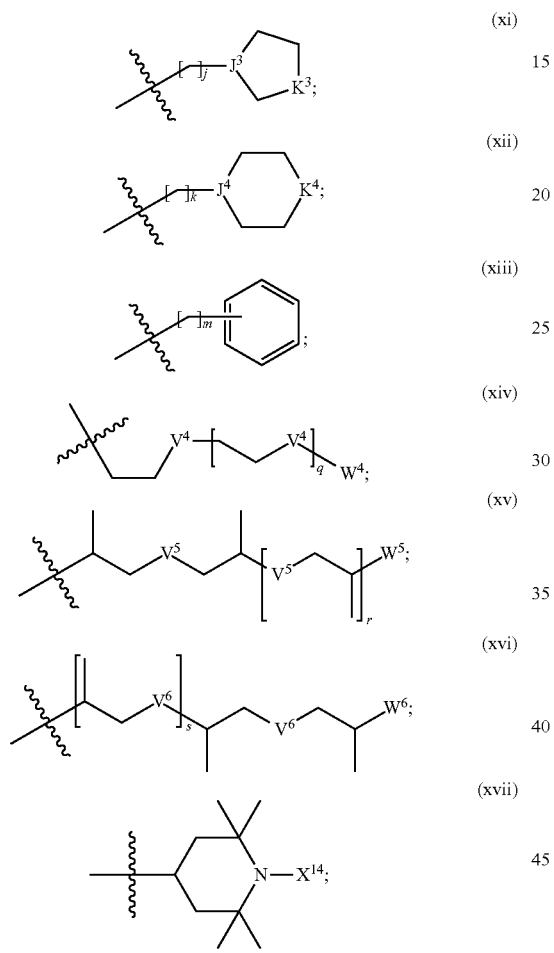

where J$^3$, J$^4$ are each independently selected from the group consisting of CH, N,
where K$^3$, K$^4$ are each independently selected from the group consisting of —O—, —NH—, —N(CH$_3$)—, —N(CH$_2$CH$_3$)—, —S—, —CH$_2$—,
where V$^4$, V$^5$, V$^6$ are each independently selected from the group consisting of —O—, —S—, —NH—, —NR'''— with R'''=unbranched or branched alkyl group having 1 to 6 carbon atoms,
where W$^4$, W$^5$, W$^6$ are each independently selected from the group consisting of H, methyl, ethyl,
where j, k, m, q, r, s are each independently an integer from the range of 0 to 50,
where X$^{14}$ is selected from the group consisting of hydrogen, —OH, —O., unbranched or branched alkyl group having 1 to 10 carbon atoms, unbranched or branched alkoxy group having 1 to 10 carbon atoms, where, in the chemical structures (xi), (xii), (xiii), (xiv), (xv), (xvi), (xvii), at least one hydrogen radical bonded to a carbon atom may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$),
and with the proviso that R$^{12}$ and R$^{17}$, when p$^{13}$=p$^{14}$=p$^{15}$=p$^{16}$=0, may each independently also be a group of the chemical structure (xviii) with

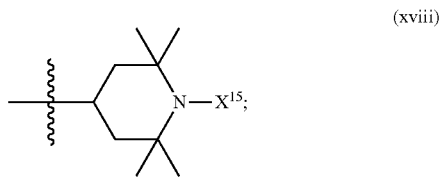

where X$^{15}$ is selected from the group consisting of hydrogen, OH, —O., unbranched or branched alkyl group having 1 to 10 carbon atoms, unbranched or branched alkoxy group having 1 to 10 carbon atoms;
and where the carbonyl compound (II) is selected from the group consisting of the chemical structures (II-A), (II-B) with

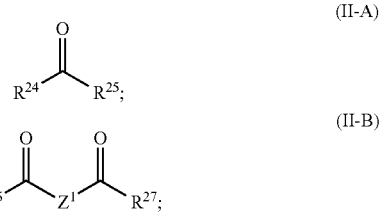

where Z$^1$ is selected from the group consisting of
direct bond,
unbranched or branched alkylene group having 1 to 30 carbon atoms,
divalent saturated hydrocarbyl group having 3 to 30 carbon atoms and having at least one saturated ring composed of 3 to 30 carbon atoms,
divalent hydrocarbyl group having 6 to 30 carbon atoms, of which at least 6 carbon atoms are present in an aromatic system and the other carbon atoms, if present, are saturated,
a bridging radical having a chemical structure selected from the group consisting of (xix), (xx) with

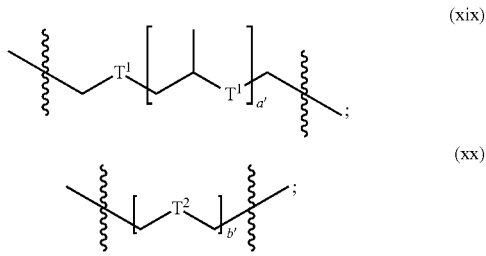

where

T$^1$, T$^2$ are each independently selected from the group consisting of —O—, —S— and —NR''''— with R''''=unbranched or branched alkyl group having 1 to 6 carbon atoms, where a' and b' are each independently an integer selected from the range of 1 to 50;

and where the R$^{24}$, R$^{25}$, R$^{26}$, R$^{27}$ radicals are selected from the group consisting of hydrogen, unbranched or branched alkyl group which has 1 to 30 carbon atoms and in which at least one hydrogen radical may be replaced by a radical selected from the group consisting of —OH, —OCH$_3$, —OCH$_2$CH$_3$, —N(CH$_3$)$_2$, —N(CH$_2$CH$_3$)$_2$, —N(CH$_3$)(CH$_2$CH$_3$), unbranched or branched alkoxy group which has 1 to 30 carbon atoms and in which at least one hydrogen radical may be replaced by a radical selected from the group consisting of —OH, —OCH$_3$, —OCH$_2$CH$_3$, —N(CH$_3$)$_2$, —N(CH$_2$CH$_3$)$_2$, —N(CH$_3$)(CH$_2$CH$_3$), a radical having a chemical structure selected from the group consisting of (xxi), (xxii), (xxiii), (xxiv), (xxv), (xxvi) with

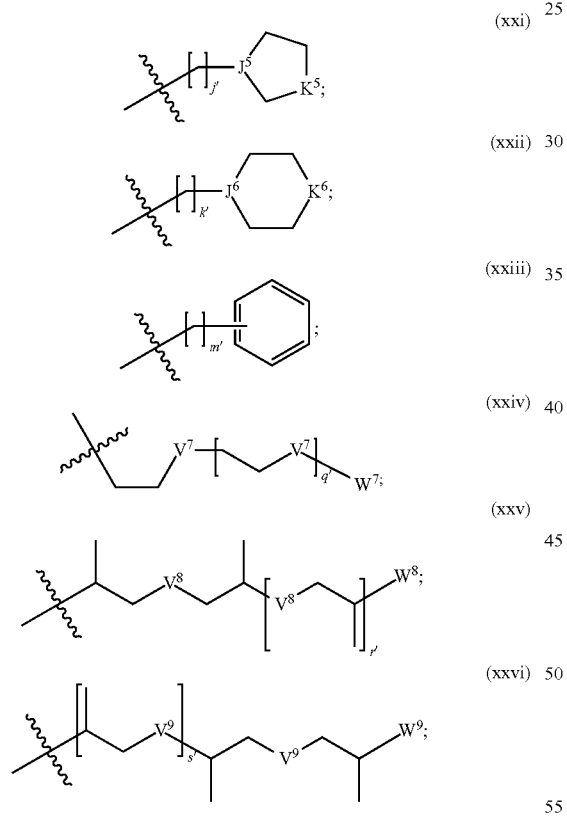

where J$^5$, J$^6$ are each independently selected from the group consisting of CH, N, where K$^5$, K$^6$ are each independently selected from the group consisting of —O—, —N(CH$_3$)—, —N(CH$_2$CH$_3$)—, —S—, —CH$_2$—, where V$^7$, V$^8$, V$^9$ are each independently selected from the group consisting of —O—, —S—, —NR''''— with R''''=unbranched or branched alkyl group having 1 to 6 carbon atoms, where W$^7$, W$^8$, W$^9$ are each independently selected from the group consisting of H, methyl, ethyl, where j', k', m', q', r', s' are each independently an integer selected from the range of 0 to 50, where, in the chemical structure (xxi), (xxii), (xxiii), (xxiv), (xxv), (xxvi), at least one hydrogen radical may be replaced by a radical selected from the group consisting of —OH, —OCH$_3$, —OCH$_2$CH$_3$, —N(CH$_3$)$_2$, —N(CH$_2$CH$_3$)$_2$, —N(CH$_3$)(CH$_2$CH$_3$);

and where R$^{24}$, R$^{25}$, R$^{26}$, R$^{27}$ are each selected independently, with the exclusion of: R$^{24}$=R$^{25}$=hydrogen.

7.2 Process according to Point 7.1, where Y$^6$, Y$^7$, Y$^8$, Y$^9$ are each independently selected from the group consisting of unbranched or branched alkylene group having 1 to 30 carbon atoms, divalent saturated hydrocarbyl group having 3 to 30 carbon atoms and having at least one saturated ring composed of 3 to 30 carbon atoms;

where Y$^6$, Y$^7$, Y$^8$, Y$^9$ are preferably each independently an unbranched or branched alkylene group having 1 to 12 carbon atoms, more preferably having 1 to 6 carbon atoms.

7.3 Process according to Point 7.1 or 7.2, where the R$^{12}$, R$^{13}$, R$^{14}$, R$^{15}$, R$^{16}$, R$^{17}$ radicals are each independently selected from the group consisting of hydrogen, unbranched or branched alkyl group having 1 to 30 carbon atoms, a group having the chemical structure (x) with

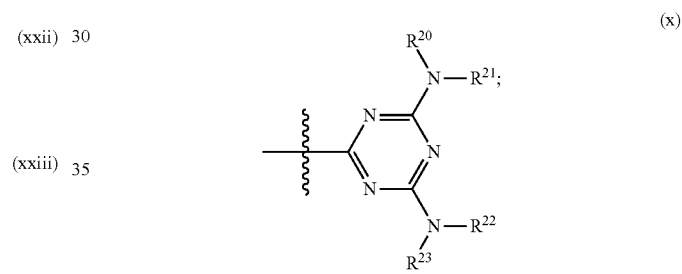

where the R$^{18}$, R$^{19}$, R$^{20}$, R$^{21}$, R$^{22}$, R$^{23}$ radicals are each independently selected from the group consisting of hydrogen, unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$), a radical having a chemical structure (xvii) with

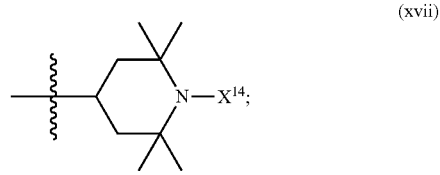

where X$^{14}$ is selected from the group consisting of hydrogen, —OH, —O., unbranched or branched alkyl group having 1 to 10 carbon atoms, unbranched or branched alkoxy group having 1 to 10 carbon atoms, and with the proviso that R$^{12}$ and R$^{17}$, when p$^{13}$=p$^{14}$=p$^{15}$=p$^{16}$=0, may each independently also be a group of the chemical structure (xviii) with

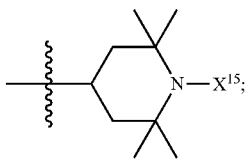

where $X^{15}$ is selected from the group consisting of hydrogen, OH, —O., unbranched or branched alkyl group having 1 to 10 carbon atoms, unbranched or branched alkoxy group having 1 to 10 carbon atoms.

7.4 Process according to one or more of Points 7.1 to 7.3, where $X^{12}=X^{14}=X^{15}$=hydrogen.

7.5 Process according to one or more of Points 7.1 to 7.4, where the $R^{12}$, $R^{13}$, $R^{14}$, $R^{15}$, $R^{16}$, $R^{17}$ radicals are each independently selected from the group consisting of hydrogen, unbranched or branched alkyl group having 1 to 12 carbon atoms, a group having the chemical structure (x) with

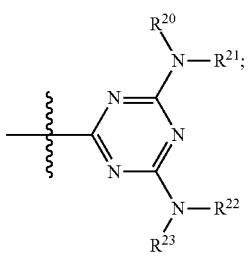

and where the $R^{18}$, $R^{19}$, $R^{20}$, $R^{21}$, $R^{22}$, $R^{23}$ radicals are each independently selected from the group consisting of hydrogen, unbranched or branched alkyl group which has 1 to 12 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$), a radical having a chemical structure (xvii) with

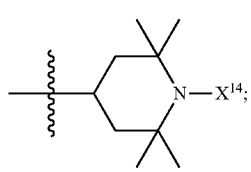

where $X^{14}$=hydrogen, and with the proviso that $R^{12}$ and $R^{17}$, when $p^{13}=p^{14}=p^{15}=p^{16}=0$, may each independently also be a group of the chemical structure (xviii) with

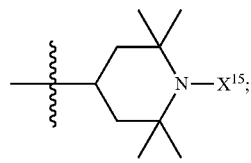

where $X^{15}$=hydrogen.

7.6 Process according to one or more of Points 7.1 to 7.5, where the $R^{12}$, $R^{13}$, $R^{14}$, $R^{15}$, $R^{16}$, $R^{17}$ radicals are each independently selected from the group consisting of unbranched or branched alkyl group having 1 to 12 carbon atoms, a group having the chemical structure (x) with

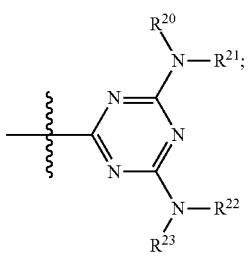

where the $R^{18}$, $R^{19}$, $R^{20}$, $R^{21}$, $R^{22}$, $R^{23}$ radicals are each independently selected from the group consisting of hydrogen, unbranched or branched alkyl group having 1 to 12 carbon atoms, a radical having a chemical structure (xvii) with

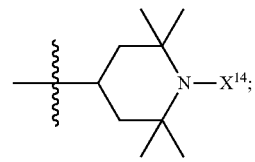

where $X^{14}$ is hydrogen, and with the proviso that $R^{12}$ and $R^{17}$, when $p^{13}=p^{14}=p^{15}=p^{16}$ 0, may each independently also be a group of the chemical structure (xviii) with

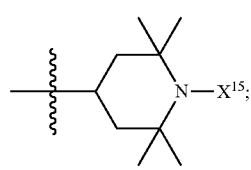

where $X^{15}$ is hydrogen.

7.7 Process according to one or more of Points 7.1 to 7.6, where $Z^1$ is selected from the group consisting of direct bond, unbranched or branched alkylene group having 1 to 30 carbon atoms, divalent saturated hydrocarbyl group having 3 to 30 carbon atoms and having at least one saturated ring composed of 3 to 30 carbon atoms.

7.8 Process according to Point 7.7, where $Z^1$ is selected from the group consisting of
direct bond,
unbranched or branched alkylene group having 1 to 12 and more preferably 1 to 6 carbon atoms.

7.9 Process according to one or more of Points 7.1 to 7.8, where the carbonyl compound (II) has the chemical structure (II-A).

7.10 Process according to Point 7.9, where
$X^{12}=X^{14}=X^{15}=$hydrogen;
and $R^{24}$, $R^{25}$ are selected from the group consisting of
hydrogen,
unbranched or branched alkyl group having 1 to 12 carbon atoms;
and where $R^{24}$, $R^{25}$ are each selected independently, with the exclusion of: $R^{24}=R^{25}=$hydrogen.

7.11 Process according to Point 7.10, where
$X^{12}=X^{14}=X^{15}=$hydrogen;
and $R^{24}$, $R^{25}$ are selected from the group consisting of
hydrogen,
unbranched or branched alkyl group having 1 to 8 carbon atoms, preferably 1 to 6 carbon atoms;
and where $R^{24}$, $R^{25}$ are each selected independently, with the exclusion of: $R^{24}=R^{25}=$hydrogen.

7.12 Process according to one or more of Points 7.1 to 7.11, wherein reductive conditions are established by reacting the at least one triacetonediamine compound (I) with the at least one carbonyl compound (II) in the presence of hydrogen and in the presence of a supported catalyst, where the supported catalyst includes at least one metal M, where the metal M is selected from the group consisting of V, Cr, Mo, Mn, Ni, Pd, Pt, Fe, Ru, Os, Co, Rh, Ir, Cu.

7.13 Process according to one or more of Points 7.1 to 7.12, which is conducted in at least one solvent, where the solvent is selected from the group consisting of aliphatic solvents, aromatic solvents, ethers, halogenated solvents, amides, thio compounds, carboxylic acids, alcohols, water.

7.14 Process according to one or more of Points 7.1 to 7.13, which is conducted at a temperature in the range from 20° C. to 350° C. and a pressure in the range from 2 bar to 500 bar.

In an eighth aspect, the invention relates to a process which is as defined under the above Points 1.1 to 1.15, 2.1 to 2.21, 3.1 to 3.20, 4.1 to 4.22, 5.1 to 5.16, 6.1 to 6.17 or 7.1 to 7.14, except that the feature
"in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$)"
is replaced by
"in which at least one hydrogen radical may be replaced by a radical selected from the group consisting of —OH, —OCH$_3$, —OCH$_2$CH$_3$, —N(CH$_3$)$_2$, —N(CH$_2$CH$_3$)$_2$, N(CH$_3$)(CH$_2$CH$_3$)";
and except that the feature
"selected from the group consisting of —O—, —NH—, —N(CH$_3$)—, —N(CH$_2$CH$_3$)—, —S—, —CH$_2$—"
is replaced by
"selected from the group consisting of —O—, —N(CH$_3$)—, —N(CH$_2$CH$_3$)—, —S—, —CH$_2$—";
and except that the feature
"selected from the group consisting of —O—, —S—, —NH— and —NR'— with R'=unbranched or branched alkyl group having 1 to 6 carbon atoms"
is replaced by
"selected from the group consisting of —O—, —S— and —NR'— with R'=unbranched or branched alkyl group having 1 to 6 carbon atoms";
and except that the feature
"selected from the group consisting of —O—, —S—, —NH—, —NR"— with R"=unbranched or branched alkyl group having 1 to 6 carbon atoms"
is replaced by
"selected from the group consisting of —O—, —S—, —NR"— with R"=unbranched or branched alkyl group having 1 to 6 carbon atoms";
and except that the feature
"selected from the group consisting of —O—, —S—, —NH—, —NR'''— with R'''=unbranched or branched alkyl group having 1 to 6 carbon atoms"
is replaced by
"selected from the group consisting of —O—, —S—, —NR'''— with R'''=unbranched or branched alkyl group having 1 to 6 carbon atoms".

General Terms

In the context of the invention, an "unbranched or branched alkyl group" is a monovalent saturated hydrocarbyl radical of the general chemical structure (a) with

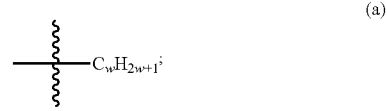

The chain of carbon atoms "—C$_w$H$_{2w+1}$" may be linear, in which case the group is an unbranched alkyl group. Alternatively, it may have branches, in which case it is a branched alkyl group.

w in the chemical structure (a) is an integer. w in an unbranched or branched alkyl group having 1 to 30 carbon atoms is selected from the range of 1 to 30. w in an unbranched or branched alkyl group having 1 to 29 carbon atoms is selected from the range of 1 to 29. w in an unbranched or branched alkyl group having 1 to 12 carbon atoms is selected from the range of 1 to 12. w in an unbranched or branched alkyl group having 1 to 10 carbon atoms is selected from the range of 1 to 10. w in an unbranched or branched alkyl group having 1 to 8 carbon atoms is selected from the range of 1 to 8. w in an unbranched or branched alkyl group having 1 to 6 carbon atoms is selected from the range of 1 to 6.

In the context of the invention, "an unbranched or branched alkyl group having 1 to 30 carbon atoms" is especially selected from methyl, ethyl, n-propyl, iso-propyl, n-butyl, sec-butyl, iso-butyl, tert-butyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosyl, n-heneicosyl, n-docosyl, n-tricosyl, n-tetracosyl, n-pentacosyl, n-hexacosyl, n-heptacosyl, n-octacosyl, n-nonacosyl, n-triacontyl.

In the context of the invention, an "unbranched or branched alkyl group having 1 to 12 carbon atoms" is especially selected from the group consisting of methyl, ethyl, n-propyl, iso-propyl, n-butyl, sec-butyl, iso-butyl, tert-butyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl, n-decyl, n-undecyl, n-dodecyl.

In the context of the invention, an "unbranched or branched alkyl group having 1 to 10 carbon atoms" is especially selected from the group consisting of methyl, ethyl, n-propyl, iso-propyl, n-butyl, sec-butyl, iso-butyl, tert-butyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl, n-decyl.

In the context of the invention, an "unbranched or branched alkyl group having 1 to 8 carbon atoms" is especially selected from the group consisting of methyl, ethyl, n-propyl, iso-propyl, n-butyl, sec-butyl, iso-butyl, tert-butyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl.

In the context of the invention, an "unbranched or branched alkyl group having 1 to 6 carbon atoms" is especially selected from the group consisting of methyl, ethyl, n-propyl, iso-propyl, n-butyl, sec-butyl, iso-butyl, tert-butyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl.

The term "unbranched or branched alkylene group" in the context of the invention denotes a divalent saturated hydrocarbyl radical which can be described by the general chemical structure (b) with

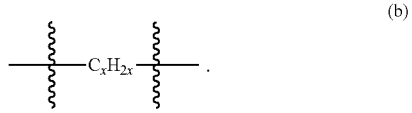

(b)

The chain of carbon atoms "—$C_xH_{2x}$—" may be linear, in which case the group is an unbranched alkylene group. Alternatively, it may have branches, in which case it is a branched alkylene group. x in the chemical structure (b) is an integer.

x in an unbranched or branched alkylene group having 1 to 30 carbon atoms is selected from the range of 1 to 30.

x in an unbranched or branched alkylene group having 1 to 12 carbon atoms is selected from the range of 1 to 12.

x in an unbranched or branched alkylene group having 1 to 6 carbon atoms is selected from the range of 1 to 6.

In the context of the invention, a "divalent saturated hydrocarbyl group having 3 to 30 carbon atoms and having at least one saturated ring composed of 3 to 30 carbon atoms" is especially a chemical structure (c) with

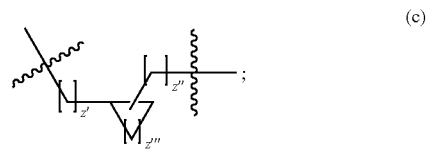

(c)

where $z'$ is an integer from 0 to 27; where $z''$ is an integer from 0 to 27; where $z'''$ is an integer from 1 to 28; and where, at the same time, $z'+z''+z''' \leq 28$.

A "divalent saturated hydrocarbyl group having 3 to 12 carbon atoms and having at least one saturated ring composed of 3 to 12 carbon atoms" in the context of the invention has a chemical structure (c) where $z'$ is an integer from 0 to 9; where $z''$ is an integer from 0 to 9; where $z'''$ is an integer from 1 to 10; and where, at the same time, $z'+z''+z''' \leq 10$.

Preferably, a "divalent saturated hydrocarbyl group having 3 to 12 carbon atoms and having at least one saturated ring composed of 3 to 12 carbon atoms" is selected from the group consisting of cyclopropylene, cyclobutylene, cyclopentylene, cyclohexylene, cycloheptylene, cyclooctylene, cyclononylene, cyclodecylene, cycloundecylene, cyclododecylene.

A "divalent saturated hydrocarbyl group having 3 to 6 carbon atoms and having at least one saturated ring composed of 3 to 6 carbon atoms" in the context of the invention has a chemical structure (c) where $z'$ is an integer from 0 to 3; where $z''$ is an integer from 0 to 3; where $z'''$ is an integer from 1 to 4; and where, at the same time, $z'+z''+z''' \leq 4$.

Preferably, a "divalent saturated hydrocarbyl group having 3 to 6 carbon atoms and having at least one saturated ring composed of 3 to 6 carbon atoms" is selected from the group consisting of cyclopropylene, cyclobutylene, cyclopentylene, cyclohexylene.

In the context of the invention, a "divalent hydrocarbyl group having 6 to 30 carbon atoms, of which at least 6 carbon atoms are present in an aromatic system and the other carbon atoms, if present, are saturated" is especially a "divalent hydrocarbyl group having 6 to 30 carbon atoms, of which 6, 10 or 14 carbon atoms are present in an aromatic system and the other carbon atoms, if present, are saturated", and is more preferably selected from the group consisting of naphthylene, anthrylene, phenanthrylene and the following chemical structure (d):

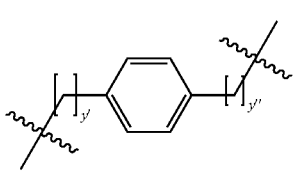

(d)

where y' is an integer from 0 to 24; where y" is an integer from 0 to 24; and where, at the same time, y'+y"≤24.

Even more preferably, it is a "divalent hydrocarbyl group having 6 to 30 carbon atoms, of which 6 or 10 carbon atoms are present in an aromatic system and the other carbon atoms, if present, are saturated", and this group is then most preferably selected from the group consisting of naphthylene and the following chemical structure (d):

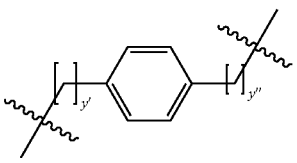

(d)

where y' is an integer from 0 to 24; where y" is an integer from 0 to 24; and where, at the same time, y'+y"≤24.

In the context of the invention, an "unbranched or branched alkoxy group" is an organic radical of the chemical structure

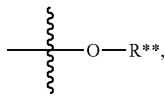

in which R** is an unbranched or branched alkyl group.

In an "unbranched or branched alkoxy group having 1 to 30 carbon atoms", R** is an unbranched or branched alkyl group having 1 to 30 carbon atoms.

In an "unbranched or branched alkoxy group having 1 to 10 carbon atoms", R** is an unbranched or branched alkyl group having 1 to 10 carbon atoms.

In the context of the invention, an "unbranched or branched alkoxy group having 1 to 10 carbon atoms" is especially selected from the group consisting of methoxy, ethoxy, n-propoxy, iso-propoxy, n-butoxy, sec-butoxy, iso-butoxy, tert-butoxy, n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy, n-heptoxy, n-octoxy, n-nonoxy, n-decoxy.

In the context of the invention, an "unbranched or branched acyl group having 1 to 30 carbon atoms" is an organic radical of the chemical structure

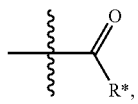

in which R* is an unbranched or branched alkyl radical having 1 to 29 carbon atoms.

More particularly, R* is selected from the group consisting of methyl, ethyl, n-propyl, iso-propyl, n-butyl, sec-butyl, iso-butyl, tert-butyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosyl, n-heneicosyl, n-docosyl, n-tricosyl, n-tetracosyl, n-pentacosyl, n-hexacosyl, n-heptacosyl, n-octacosyl, n-nonacosyl.

"—O." in the context of the invention denotes an oxygen-centred free-radical.

In the context of the invention, the wording "at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$)" means that the group in question is in unsubstituted form or, in the group in question, at least one hydrogen radical bonded to a carbon atom, preferably 1 to 5, more preferably 1 to 3 and most preferably 1 to 2 hydrogen radical(s) bonded to the same or different carbon atom(s), is/are replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$).

In the context of the invention, the wording "at least one hydrogen radical may be replaced by a radical selected from the group consisting of —OH, —OCH$_3$, —OCH$_2$CH$_3$, —N(CH$_3$)$_2$, —N(CH$_2$CH$_3$)$_2$, —N(CH$_3$)(CH$_2$CH$_3$)" means that the group in question is in unsubstituted form or, in the group in question, at least one hydrogen radical bonded to a carbon atom, preferably 1 to 5, more preferably 1 to 3 and most preferably 1 to 2 hydrogen radical(s) bonded to the same or different carbon atom(s), is/are replaced by a radical selected from the group consisting of —OH, —OCH$_3$, —OCH$_2$CH$_3$, —N(CH$_3$)$_2$, —N(CH$_2$CH$_3$)$_2$, —N(CH$_3$)(CH$_2$CH$_3$).

Process According to the Invention

The process according to the invention is a reductive amination in which the carbonyl group in the carbonyl compound (II) reacts with a nitrogen atom in the triacetonediamine compound (I). This involves replacement of a hydrogen radical in a primary or secondary amine group in the triacetonediamine compound (I) by the organic radical in the carbonyl compound (II) bonded to the oxygen atom of the carbonyl group. The N-substituted triacetonediamine compound is thus the reaction product of the reductive amination of a primary or secondary amine group in the triacetonediamine compound (I) with a carbonyl group of the carbonyl compound (II).

The process according to the invention surprisingly solves the disadvantages discussed in the prior art processes: Thus, the process according to the invention proceeds from triacetonediamine or a triacetonediamine compound. In this way, the process according to the invention avoids the use of the unstable triacetonamine reactant, such that the presence thereof in the resulting product mixture is ruled out from the outset and the inadequate colour stability of the products that occurs in the prior art processes is drastically improved.

In addition, by means of the process according to the invention, compared to the conventional processes, higher yields of triacetonediamine compounds are also possible. The process according to the invention also enables the preparation of triacetonediamine compounds bearing branched alkyl radicals on the exocyclic nitrogen atom—such triacetonediamine compounds are obtainable by the prior art processes in much poorer yields. Moreover, compounds disubstituted on the exocyclic nitrogen atom are also more easily obtainable by the process according to the invention.

For example, a TAD compound (I) of the chemical structure (I-A) would react with a carbonyl compound (II) of the structure (II-A) in the process according to the invention, in the case of equimolar use of (I-A) and (II-A), as follows:

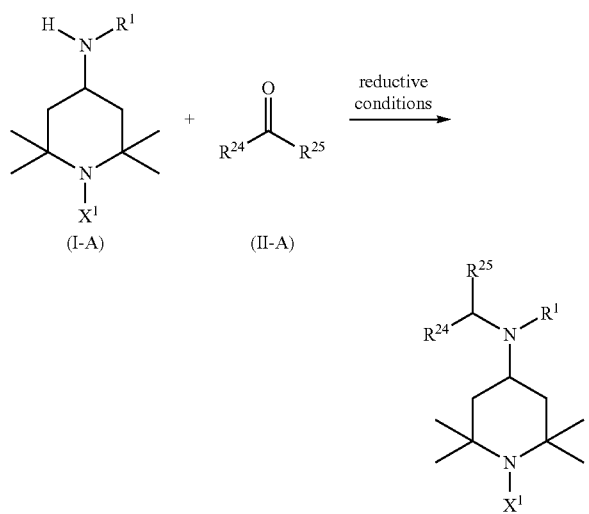

It will be apparent that, in the case of a molar excess of carbonyl compound (II) in relation to triacetonediamine compound (I) (if the latter has two or more aminic groups), it is also possible for further primary and/or secondary amine groups in this triacetonediamine compound (I) to undergo a reductive amination in the sequence of their reactivity or for a primary amine group in the triacetonediamine compound (I) to undergo such a reaction twice.

It will likewise be apparent that, in the case of a molar excess of triacetonediamine compound (I) in relation to carbonyl compound (II) [if it has two or more carbonyl groups, as is the case, for example, in the chemical structures (II-B) or (II-C)], further carbonyl groups in the carbonyl compound (II) would also undergo a reductive amination in the sequence of their reactivity.

Even more specific substitution of hydrogen atoms on the 4-amino group of the 2,2,6,6-tetramethylpiperidinyl radical in the triacetonediamine compound (I) is possible when the process according to the invention is conducted as described in the eighth aspect.

The process according to the invention can be conducted without solvent or else in at least one solvent, preferably in at least one solvent. Suitable solvents are all solvents in which the reactants have good solubility and which also do not have any disruptive influence on the process according to the invention. More particularly, the solvent is selected from the group consisting of aliphatic solvents, aromatic solvents, ethers, halogenated solvents, amides, thio compounds, carboxylic acids, alcohols, water; preferably, the solvent is selected from the group consisting of aliphatic solvents, aromatic solvents, ethers, alcohols, water; more preferably, the solvent is selected from the group consisting of ethers, alcohols, water; even more preferably, the solvent is selected from the group consisting of alcohols (for example methanol), water.

Aliphatic solvents are especially selected from the group consisting of pentane, hexane, heptane, octane, decane, cyclopentane, cyclohexane, methylcyclohexane, petroleum ether.

Aromatic solvents are especially selected from the group consisting of benzene, toluene, xylene, ethylbenzene, cumene, bromobenzene, chlorobenzene, dichlorobenzene, furan.

Ethers are especially selected from the group consisting of diethyl ether, dipropyl ether, dibutyl ether, methyl tert-butyl ether, ethylene glycol monomethyl ether, ethylene glycol monoethyl ether, ethylene glycol dimethyl ether, ethylene glycol diethyl ether, diethylene glycol monomethyl ether, diethylene glycol monoethyl ether, diethylene glycol dimethyl ether, diethylene glycol diethyl ether, triethylene glycol monomethyl ether, triethylene glycol monoethyl ether, triethylene glycol dimethyl ether, triethylene glycol diethyl ether, polyethylene glycol monomethyl ether, polyethylene glycol monoethyl ether, polyethylene glycol dimethyl ether, polyethylene glycol diethyl ether, 1,4-dioxane, 1,3-dioxane, tetrahydrofuran.

Halogenated solvents are especially selected from the group consisting of dichloromethane, chloroform, tetrachloromethane.

Amides are especially selected from the group consisting of dimethylformamide, dimethylacetamide.

Thio compounds are especially selected from the group consisting of dimethyl sulphoxide, sulpholane.

Carboxylic acids are especially selected from the group consisting of formic acid, acetic acid, propionic acid, butanoic acid, pentanoic acid.

Alcohols are especially selected from the group consisting of methanol, ethanol, propanol, iso-propanol, propane-1,2-diol, propane-1,3-diol, glycerol, butanol, sec-butanol, iso-butanol, tert-butanol, butane-1,2-diol, butane-1,3-diol, butane-1,4-diol, pentan-1-ol, pentan-2-ol, pentan-3-ol, tert-amyl alcohol, pentane-1,2-diol, pentane-1,3-diol, pentane-1,4-diol, pentane-1,5-diol, cyclopentanol, hexanol, cyclohexanol, heptanol, octanol, nonanol, decanol, ethylene glycol, diethylene glycol, triethylene glycol, polyethylene glycol, benzyl alcohol, phenol; preferably selected from methanol, ethanol, n-propanol, iso-propanol.

The ratio of the molar amounts of reactants used is not restricted in principle and depends on how many alkyl radicals are to be introduced at how many nitrogen atoms in the TAD derivative (I).

For example, in the case of reaction of TAD with a carbonyl compound (II) of the chemical structure (II-A), an equimolar amount, based on the NH functions to be substituted, of (II-A) can be used.

In the case of reaction of TAD (when the exocyclic 4-amino group is to be substituted) with a carbonyl compound (II) of the chemical structure (II-A), the result would be the following reaction:

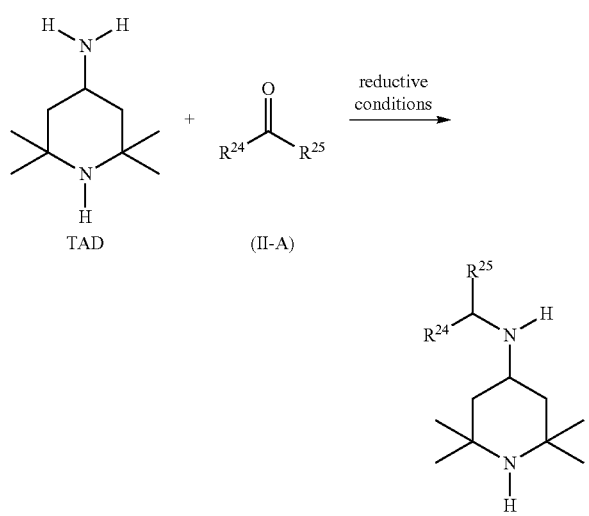

In the case of reaction of a triacetonediamine compound (I) with a carbonyl compound (II) of the chemical structure (II-A), preferably 0.8 to 2.0 molar equivalents of the compound (II-A) are used per NH function to be substituted in the triacetonediamine compound (I), more preferably 0.8 to 1.5 molar equivalents, even more preferably 0.8 to 1.3 molar equivalents and most preferably 0.9 to 1.2 molar equivalents of the compound (II-A) per NH function to be substituted in the triacetonediamine compound (I).

In the case of reaction of a triacetonediamine compound (I) with a carbonyl compound (II) of the chemical structure (II-B), preferably 0.4 to 1.0 molar equivalent of the compound (II-B) is used per NH function to be substituted in the triacetonediamine compound (I), more preferably 0.4 to 0.75 molar equivalent, even more preferably 0.4 to 0.65 molar equivalent and most preferably 0.45 to 0.6 molar equivalent of the compound (II-B) per NH function to be substituted in the triacetonediamine compound (I).

In the case of reaction of a triacetonediamine compound (I) with a carbonyl compound (II) of the chemical structure (II-C), preferably 0.27 to 0.67 molar equivalent of the compound (II-C) is used per NH function to be substituted in the triacetonediamine compound (I), more preferably 0.27 to 0.5 molar equivalent, even more preferably 0.27 to 0.43 molar equivalent and most preferably 0.3 to 0.4 molar equivalent of the compound (II-C) per NH function to be substituted in the triacetonediamine compound (I).

The process according to the invention is conducted under reductive conditions. "Reductive conditions" are understood to mean the conditions under which the imine shown in the reaction scheme <1> is converted to the corresponding amine by addition of hydrogen.

Preferably, in the process according to the invention, reductive conditions are established by reacting the at least one triacetonediamine compound (I) with the at least one carbonyl compound (II) in the presence of hydrogen and in the presence of a supported catalyst, where the supported catalyst includes at least one metal M, where the metal M is selected from the group consisting of V, Cr, Mo, Mn, Ni, Pd, Pt, Fe, Ru, Os, Co, Rh, Ir, Cu; preferably selected from the group consisting of V, Cr, Mo, Mn, Ni, Pd, Pt, Fe, Ru, Os, Co, Rh, Ir, Cu; more preferably selected from the group consisting of Cr, Mo, Mn, Ni, Pd, Pt, Ru, Rh; even more preferably selected from the group consisting of Cr, Ni, Pd, Pt; most preferably selected from the group consisting of Ni, Pd.

The process according to the invention can be conducted continuously or non-continuously, i.e. batchwise.

The reaction time depends on the progress of the process and on the desired conversion—the aim is typically a maximum possible conversion and the process according to the invention is continued until no further conversion of reactant can be observed.

The temperature in the process according to the invention is not restricted and is preferably in the range from 20° C. to 350° C., more preferably in the range from 50° C. to 300° C., even more preferably in the range from 50° C. to 250° C., most preferably in the range from 70° C. to 200° C.

The pressure in the process according to the invention is not restricted and is preferably in the range from 2 bar to 500 bar, more preferably in the range from 5 bar to 350 bar, even more preferably in the range from 25 bar to 300 bar.

The above temperature ranges and pressure ranges may of course also be present in combination. Thus, the process can preferably be conducted at a temperature in the range from 20° C. to 350° C. [more preferably in the range from 50° C. to 300° C., even more preferably in the range from 50° C. to 250° C., most preferably in the range from 70° C. to 200° C.] and a pressure in the range from 2 bar to 500 bar [preferably in the range from 2 bar to 500 bar, more preferably in the range from 5 bar to 350 bar, even more preferably in the range from 25 bar to 300 bar].

The process according to the invention solves the above problem in a completely surprising manner: As apparent from the Examples section, the products prepared by the process according to the invention have higher colour stability than the TAD compounds obtained by the prior art process. This can be verified in that the N-substituted TAD compounds obtained by the process according to the invention, both directly after the preparation and, more particularly, after storage, have a lower Hazen colour number than the same TAD compounds synthesized by the conventional processes. The Hazen colour number can be determined as described in DIN EN ISO 6271 (2005).

Having generally described this invention, a further understanding can be obtained by reference to certain specific examples which are provided herein for purposes of illustration only, and are not intended to be limiting unless otherwise specified.

The examples which follow are intended to illustrate the invention in detail, without any intention that the invention be restricted to these embodiments.

EXAMPLES

Comparative Examples C1-C5

A 2 l pressure autoclave was preheated to 40° C. by means of a thermostat. Then 125 ml of methanol and 388.1 g (2.5 mol) of TAA were added to the reactor and stirred. Thereafter, 2.5 mol of the amine (experiment C1: n-propylamine; experiment C2: n-butylamine; experiment C3: sec-butylamine; experiment C4: iso-propylamine; experiment C5: n-octylamine) were added and rinsed in with 125 ml of methanol. The catalyst (10% by weight of Pd on activated carbon, 2.7 mmol based on Pd; catalyst used: "E 196 NN/W 10%" from Evonik Industries AG) was added and the reactor was closed.

Hydrogen was injected while stirring (20 bar $H_2$) and an internal autoclave temperature of 80° C. was set. Hydrogenation was effected at a pressure of 20-30 bar until no significant uptake of hydrogen was observed any longer.

The reactor was then cooled and decompressed. The crude product was discharged and filtered, and then the solvent was first removed (80-120° C., standard pressure). The residue was subsequently purified by means of a vacuum distillation using a 0.5 m column having random packing.

The purity of the distilled product was determined by gas chromatography (Agilent 5890 or 7890, FID detector).

In addition, the colour stability of the products obtained was examined by storage in closed sample tubes and checking of the Hazen colour number. This was done using the following intervals:
a) after distillation;
b) after storage at 70° C. for 7 days;
c) after storage at room temperature for 30 days;
d) after storage at room temperature for 6 months.
The results are compiled in Table 1.

Inventive Examples I1-I5

A 2 l pressure autoclave was preheated to 40° C. by means of a thermostat. Then 125 ml of methanol and 390.7 g (2.5 mol) of TAD were added to the reactor and stirred. Thereafter, 2.5 mol of the carbonyl compound (experiment I1: propanal; experiment I2: butanal; experiment I3: butanone; experiment I4: acetone; experiment I5: octanal) were added and rinsed in with 125 ml of methanol. The catalyst (10% by weight of Pd on activated carbon, 2.7 mmol based on Pd; catalyst used: "E 196 NN/W 10%" from Evonik Industries AG) was added and the reactor was closed.

Hydrogen was injected while stirring (20 bar $H_2$) and an internal autoclave temperature of 80° C. was set. Hydrogenation was effected at a pressure of 20-30 bar until no significant uptake of hydrogen was observed any longer.

The reactor was then cooled and decompressed. The crude product was discharged and filtered, and then the solvent was first removed (80-120° C., standard pressure). The residue was subsequently purified by means of a vacuum distillation using a 0.5 m column having random packing.

The purity of the distilled product was determined by gas chromatography (Agilent 5890 or 7890, FID detector).

In addition, the colour stability of the products obtained was examined by storage in closed sample tubes and checking of the Hazen colour number. This was done using the following intervals:
a) after distillation;
b) after storage at 70° C. for 7 days;
c) after storage at room temperature for 30 days;
d) after storage at room temperature for 6 months.
The results are compiled in Table 2.

Results

On comparison of the comparative examples with the inventive examples, the following surprising effects were found:

The comparison of C1 with I1, C2 with I2, C5 with I5 shows that the colour stability of the triacetonediamine compounds obtained in experiments I1, I2 and I5 is distinctly increased compared to the same triacetonediamine compounds obtained with C1, C2 and C5 (apparent from the smaller colour numbers observed in I1, I2 and I5 compared to C1, C2 and C5).

While it was not possible to obtain any product at all in the case of C3 and C4 with the conventional processes, the process according to the invention, as apparent from examples I3 and I4, allows synthesis of the corresponding triacetonediamine compounds with good yield.

TABLE 1

| Example number | Amine used | Hydrogenation time | Product | Yield in g (% based on 2.5 mol of TAA used) | Colour number (Hazen) Day 1 | 7 d, 70° C. | 30 d, RT | 0.5 a, RT |
|---|---|---|---|---|---|---|---|---|
| C1 | n-Propylamine | 5 hours, 30 minutes | (structure) | 167.0 g (33.7%) Purity: 98.2% | 390 | 1390 | 351 | 243 |
| C2 | n-Butylamine | 4 hours | (structure) | 355.7 g (67.0%) Purity 98.7% | 146 | 617 | 320 | 234 |

TABLE 1-continued

| Example number | Amine used | Hydrogenation time | Product | Yield in g (%) based on 2.5 mol of TAA used | Colour number (Hazen) Day 1 | 7 d, 70° C. | 30 d, RT | 0.5 a, RT |
|---|---|---|---|---|---|---|---|---|
| C3 | sec-Butylamine | 13 hours | [structure: 4-(sec-butylamino)-2,2,6,6-tetramethylpiperidine] | No yield detected | — | — | — | — |
| C4 | iso-Propylamine | 11 hours, 30 minutes | [structure: 4-(isopropylamino)-2,2,6,6-tetramethylpiperidine] | No yield detected | — | — | — | — |
| C5 | n-Octylamine | 4 hours, 20 minutes | [structure: 4-(n-octylamino)-2,2,6,6-tetramethylpiperidine] | 598.0 g (89.1%) Purity: 99.7% | 60 | 321 | 124 | 61 |

TABLE 2

| Example number | Aldehyde/ketone used | Hydrogenation time | Product | Yield in g (%) based on 2.5 mol of TAA used | Colour number (Hazen) Day 1 | 7 d, 70° C. | 30 d, RT | 0.5 a, RT |
|---|---|---|---|---|---|---|---|---|
| I1 | Propanal | 5 hours | [structure: 4-(n-propylamino)-2,2,6,6-tetramethylpiperidine] | 188.1 g (37.9%) Purity 97.8% | 73 | 382 | 166 | 93 |
| I2 | Butanal | 5 hours, 30 minutes | [structure: 4-(n-butylamino)-2,2,6,6-tetramethylpiperidine] | 208.3 g (39.2%) Purity: 92.7% | 91 | 290 | 135 | 70 |

TABLE 2-continued

| Example number | Aldehyde/ketone used | Hydrogenation time | Product | Yield in g (% based on 2.5 mol of TAA used) | Colour number (Hazen) | | | |
|---|---|---|---|---|---|---|---|---|
| | | | | | Day 1 | 7 d, 70° C. | 30 d, RT | 0.5 a, RT |
| I3 | Butanone | 18 hours | 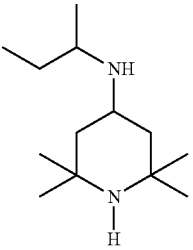 | 244.0 g (46.0%) Purity: 97.3% | 41 | 96 | 23 | 23 |
| I4 | Acetone | 15 hours | 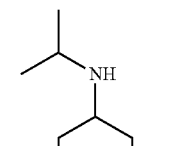 | 316.7 g (63.9%) Purity: 95.3% | 37 | 80 | 36 | 30 |
| I5 | Octanal | 3 hours, 30 minutes | 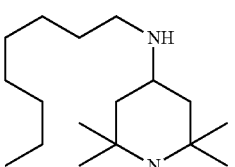 | 513.0 g (76.5%) Purity: 99.9% | 5 | 51 | 10 | 14 |

European patent application 15152070.7 filed Jan. 22, 2015, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A process for preparing an N-substituted triacetonediamine compound, comprising:
   reacting at least one triacetonediamine compound (I) with at least one carbonyl compound (II) under reductive conditions to obtain the N-substituted triacetonediamine compound,
   wherein the triacetonediamine compound (I) is selected from the group consisting of the chemical structures (I-A), (I-B), (I-C), (I-D), and (I-E):

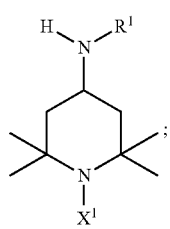

(I-A)

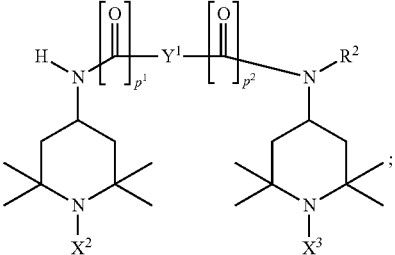

(I-B)

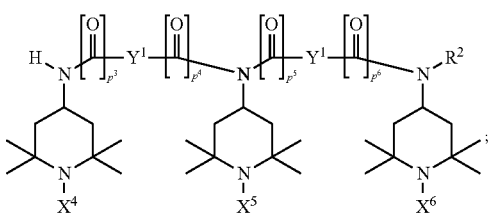

(I-C)

-continued

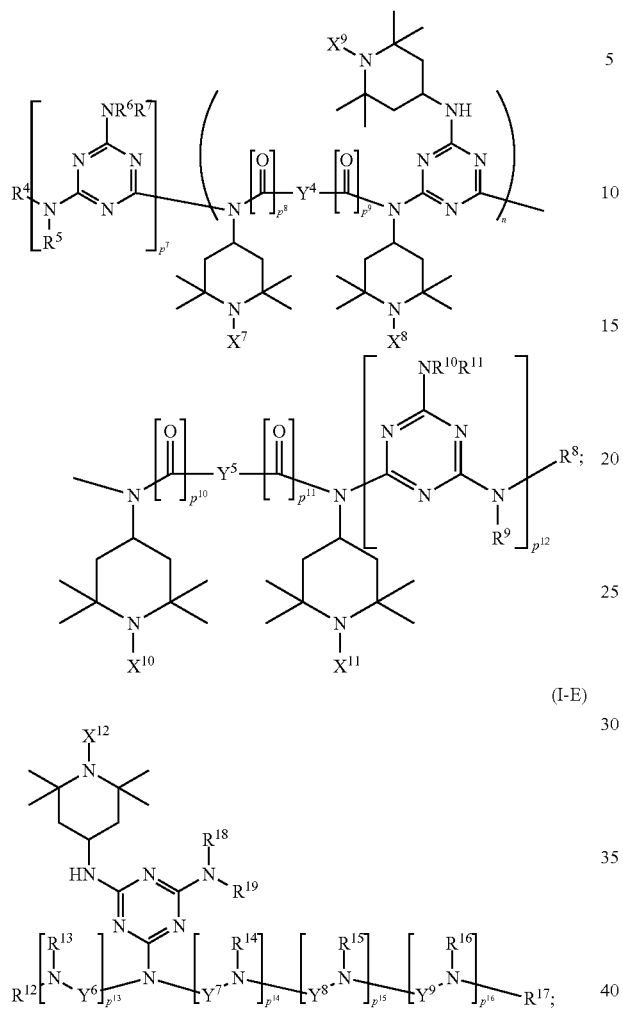

(I-D)

(I-E)

wherein the carbonyl compound (II) is selected from the group consisting of the chemical structures (II-A), (II-B), and (II-C):

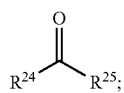

(II-A)

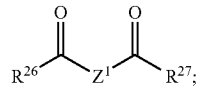

(II-B)

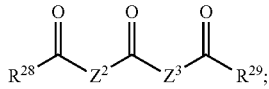

(II-C)

and wherein reductive conditions are established by reacting the at least one triacetonediamine compound (I) with the at least one carbonyl compound (II) in the presence of hydrogen and in the presence of a supported catalyst, wherein the supported catalyst comprises at least one metal M, wherein the metal M is selected from the group consisting of V, Cr, Mo, Mn, Ni, Pd, Pt, Fe, Ru, Os, Co, Rh, Ir, and Cu, wherein in chemical structures (I-A), (I-B), (I-C), (I-D), and (I-E):

n is an integer from the range of 1 to 20:

wherein $p^1, p^2, p^3, p^4, p^5, p^6, p^7, p^8, p^9, p^{10}, p^{11}, p^{12}, p^{13}, p^{14}, p^{15}, p^{16}$ are each independently 0 or 1;

wherein $X^1, X^2, X^3, X^4, X^5, X^6, X^7, X^8, X^9, X^{10}, X^{11}, X^{12}$ are each independently selected from the group consisting of hydrogen, OH, —O., unbranched or branched alkyl group having 1 to 10 carbon atoms, and unbranched or branched alkoxy group having 1 to 10 carbon atoms;

wherein $Y^1, Y^2, Y^3, Y^4, Y^5, Y^6, Y^7, Y^8, Y^9$ are each independently selected from the group consisting of unbranched or branched alkylene group having 1 to 30 carbon atoms, divalent saturated hydrocarbyl group having 3 to 30 carbon atoms and having at least one saturated ring comprising 3 to 30 carbon atoms, divalent hydrocarbyl group having 6 to 30 carbon atoms, of which at least 6 carbon atoms are present in an aromatic system and the other carbon atoms, if present, are saturated, and a bridging radical having a chemical structure selected from the group consisting of (i), (ii) with

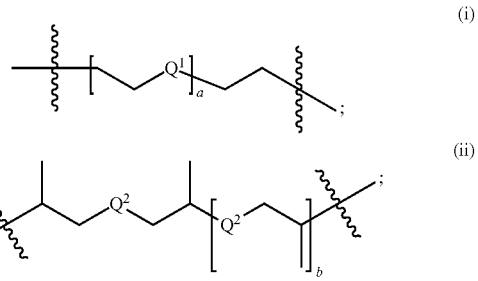

wherein $Q^1, Q^2$ are each independently selected from the group consisting of —O—, —S—, —NH— and —NR'— with R'=unbranched or branched alkyl group having 1 to 6 carbon atoms, wherein a is an integer selected from the range of 1 to 50, wherein b is an integer selected from the range of 0 to 50, and wherein $Y^1$, if at least one of $p^1$ and $p^2$ has the value of 1, is selected from the list above including a direct bond, and wherein $Y^2$, if at least one of $p^3$ and $p^4$ has the value of 1, is selected from the list above including a direct bond, and wherein $Y^3$, if at least one of $p^5$ and $p^6$ has the value of 1, is selected from the list above including a direct bond, and wherein $Y^4$, if at least one of $p^7$ and $p^8$ has the value of 1, is selected from the list above including a direct bond, and wherein $Y^5$, if at least one of $p^9$ and $p^{10}$ has the value of 1, is selected from the list above including a direct bond, wherein the $R^1, R^2, R^3, R^4, R^5, R^6, R^1, R^8, R^9, R^{10}, R^{11}$ radicals are each independently selected from the group consisting of hydrogen,
unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, and —N(CH$_3$)(CH$_2$CH$_3$),
unbranched or branched acyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, and —N(CH$_3$)(CH$_2$CH$_3$), and
a radical having a chemical structure selected from the group consisting of (iii), (iv), (v), (vi), (vii), (viii), and (ix) with

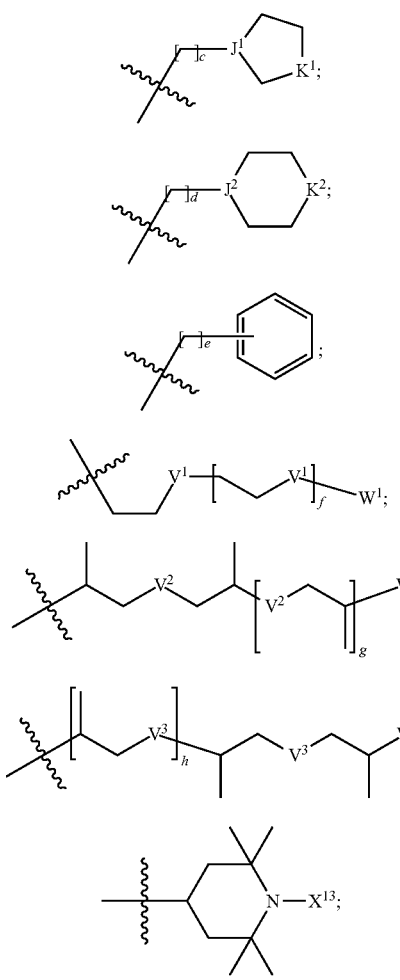

wherein $J^1$, $J^2$ are each independently selected from the group consisting of CH, and N,
wherein $K^1$, $K^2$ are each independently selected from the group consisting of —O—, —NH—, —N(CH$_3$)—, —N(CH$_2$CH$_3$)—, —S—, and —CH$_2$—,
wherein $V^1$, $V^2$, $V^3$ are each independently selected from the group consisting of —O—, —S—, —NH—, and —NR"— with R"=unbranched or branched alkyl group having 1 to 6 carbon atoms,
wherein $W^1$, $W^2$, $W^3$ are each independently selected from the group consisting of H, methyl, and ethyl,
wherein c, d, e, f, g, h are each independently an integer from the range of 0 to 50,
wherein $X^{13}$ is selected from the group consisting of hydrogen, —OH, —O., unbranched or branched alkyl group having 1 to 10 carbon atoms, and unbranched or branched alkoxy group having 1 to 10 carbon atoms,
wherein, in the chemical structures (iii), (iv), (v), (vi), (vii), (viii), and (ix), at least one hydrogen radical bonded to a carbon atom may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, and —N(CH$_3$)(CH$_2$CH$_3$);
wherein the $R^{12}$, $R^{13}$, $R^{14}$, $R^{15}$, $R^{16}$, $R^{17}$ radicals are each independently selected from the group consisting of
hydrogen,
unbranched or branched alkyl group having 1 to 30 carbon atoms, and
a group having the chemical structure (x) with

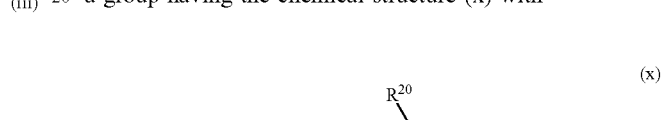

wherein the $R^{18}$, $R^{19}$, $R^{20}$, $R^{21}$, $R^{22}$, $R^{23}$ radicals are each independently selected from the group consisting of
hydrogen,
unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, and —N(CH$_3$)(CH$_2$CH$_3$),
unbranched or branched acyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, and —N(CH$_3$)(CH$_2$CH$_3$), and
a radical having a chemical structure selected from the group consisting of (xi), (xii), (xiii), (xiv), (xv), (xvi), and (xvii) with

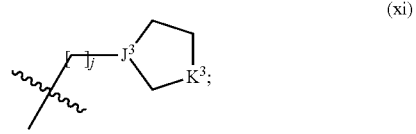

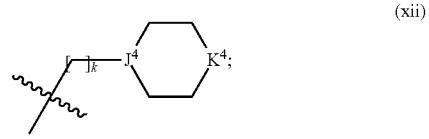

-continued

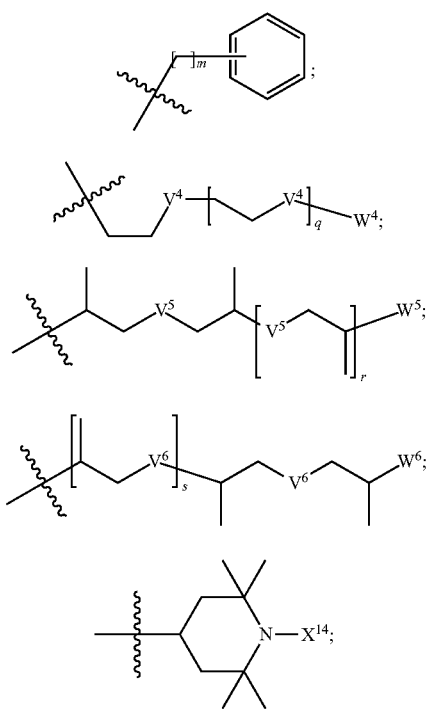

wherein J³, J⁴ are each independently selected from the group consisting of CH, and N, wherein K³, K⁴ are each independently selected from the group consisting of —O—, —NH—, —N(CH₃)—, —N(CH₂CH₃)—, —S—, and —CH₂—, wherein V⁴, V⁵, V⁶ are each independently selected from the group consisting of —O—, —S—, —NH—, and —NR'''— with R'''=unbranched or branched alkyl group having 1 to 6 carbon atoms, wherein W⁴, W⁵, W⁶ are each independently selected from the group consisting of H, methyl, and ethyl, wherein j, k, m, q, r, s are each independently an integer from the range of 0 to 50, wherein X¹⁴ is selected from the group consisting of hydrogen, —OH, —O—, unbranched or branched alkyl group having 1 to 10 carbon atoms, and unbranched or branched alkoxy group having 1 to 10 carbon atoms, where, in the chemical structures (xi), (xii), (xiii), (xiv), (xv), (xvi), and (xvii), at least one hydrogen radical bonded to a carbon atom may be replaced by a radical selected from the group consisting of —OH, —NH₂, —OCH₃, —OCH₂CH₃, —NH(CH₃), —N(CH₃)₂, —NH(CH₂CH₃), —N(CH₂CH₃)₂, and —N(CH₃)(CH₂CH₃), and with the proviso that R¹² and R¹⁷, if p¹³=p¹⁴=p¹⁵=p¹⁶=0, are each independently selected from the list above including a group of the chemical structure (xviii) with

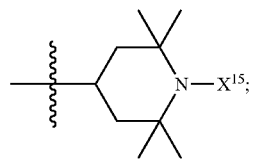

wherein X¹⁵ is selected from the group consisting of hydrogen, OH, —O., unbranched or branched alkyl group having 1 to 10 carbon atoms, and unbranched or branched alkoxy group having 1 to 10 carbon atoms;

and wherein in chemical structures (II-A), (II-B), and II-C)

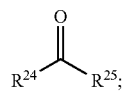

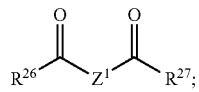

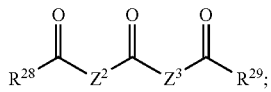

Z¹, Z², Z³ are each independently selected from the group consisting of direct bond, unbranched or branched alkylene group having 1 to 30 carbon atoms, divalent saturated hydrocarbyl group having 3 to 30 carbon atoms and having at least one saturated ring comprising 3 to 30 carbon atoms, divalent hydrocarbyl group having 6 to 30 carbon atoms, of which at least 6 carbon atoms are present in an aromatic system and the other carbon atoms, if present, are saturated, and a bridging radical having a chemical structure selected from the group consisting of (xix), and (xx) with

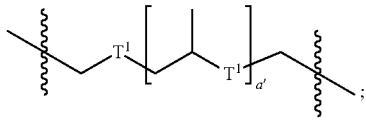

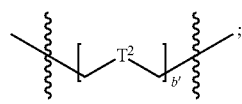

wherein

T¹, T² are each independently selected from the group consisting of —O—, —S— and —NR''''— with R''''=unbranched or branched alkyl group having 1 to 6 carbon atoms, wherein a' and b' are each independently an integer selected from the range of 1 to 50;

and wherein the R²⁴, R²⁵, R²⁶, R²⁷, R²⁸, R²⁹ radicals are selected from the group consisting of hydrogen, unbranched or branched alkyl group which has 1 to 30 carbon atoms and in which at least one hydrogen radical may be replaced by a radical selected from the group consisting of —OH, —OCH$_3$, —OCH$_2$CH$_3$, —N(CH$_3$)$_2$, —N(CH$_2$CH$_3$)$_2$, —N(CH$_3$)(CH$_2$CH$_3$), a radical having a chemical structure selected from the group consisting of (xxi), (xxii), (xxiii), (xxiv), (xxv), and (xxvi):

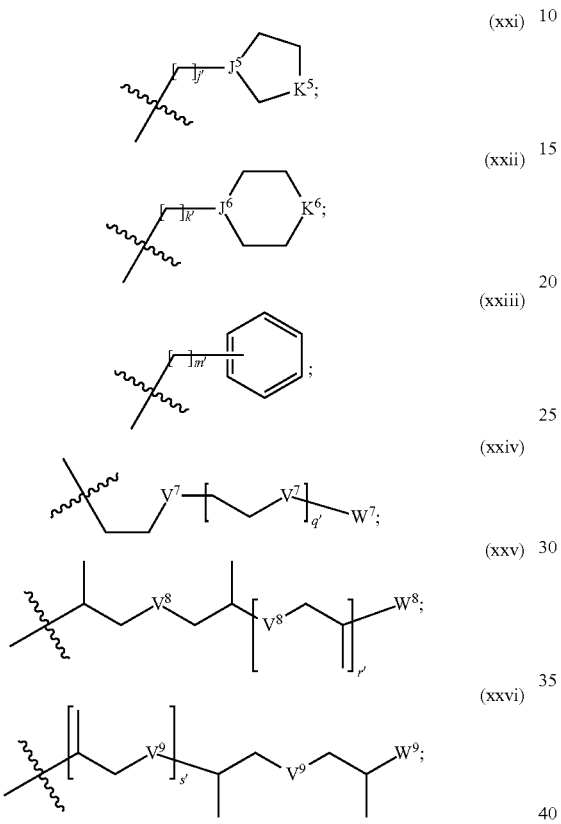

(xxi)

(xxii)

(xxiii)

(xxiv)

(xxv)

(xxvi)

wherein $J^5$, $J^6$ are each independently selected from the group consisting of CH, and N, wherein $K^5$, $K^6$ are each independently selected from the group consisting of —O—, —N(CH$_3$)—, —N(CH$_2$CH$_3$)—, —S—, and —CH$_2$—, wherein $V^7$, $V^8$, $V^9$ are each independently selected from the group consisting of —O—, —S—, and —NR''''— with R''''=unbranched or branched alkyl group having 1 to 6 carbon atoms, wherein $W^7$, $W^8$, $W^9$ are each independently selected from the group consisting of H, methyl, and ethyl, wherein j', k', m', q', r', s' are each independently an integer selected from the range of 0 to 50, wherein, in the chemical structure (xxi), (xxii), (xxiii), (xxiv), (xxv), (xxvi), at least one hydrogen radical may be replaced by a radical selected from the group consisting of —OH, —OCH$_3$, —OCH$_2$CH$_3$, —N(CH$_3$)$_2$, —N(CH$_2$CH$_3$)$_2$, and —N(CH$_3$)(CH$_2$CH$_3$);

and wherein $R^{24}$, $R^{25}$, $R^{26}$, $R^{27}$, $R^{28}$, $R^{29}$ are each selected independently, with the exclusion of: $R^{24}$=$R^{25}$=hydrogen.

2. The process according to claim 1, wherein $p^1$=$p^2$=$p^3$=$p^4$=$p^5$=$p^6$=$p^8$=$p^9$=$p^{10}$=$p^{11}$=0 and wherein $p^7$, $p^{12}$, $p^{13}$, $p^{14}$, $p^{15}$, $p^{16}$ are each independently 0 or 1.

3. The process according to claim 1, wherein $Y^1$, $Y^2$, $Y^3$, $Y^4$, $Y^5$, $Y^6$, $Y^7$, $Y^8$, $Y^9$ are each independently selected from the group consisting of an unbranched alkylene group having 1 to 30 carbon atoms, a branched alkylene group having 1 to 30 carbon atoms, and a divalent saturated hydrocarbyl group having 3 to 30 carbon atoms and having at least one saturated ring comprising 3 to 30 carbon atoms.

4. The process according to claim 1, wherein the $R^1$, $R^2$, $R^3$, $R^4$, $R^5$, $R^6$, $R^7$, $R^8$, $R^9$, $R^{10}$, $R^{11}$ radicals are each independently selected from the group consisting of hydrogen, unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, and —N(CH$_3$)(CH$_2$CH$_3$), and a radical having a chemical structure (ix)

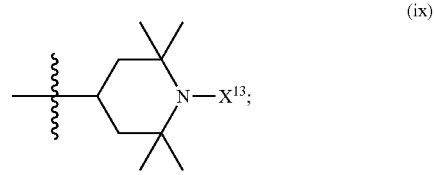

(ix)

wherein $X^{13}$ is selected from the group consisting of hydrogen, —OH, —O., unbranched or branched alkyl group having 1 to 10 carbon atoms, and unbranched or branched alkoxy group having 1 to 10 carbon atoms;

and wherein the $R^{12}$, $R^{13}$, $R^{14}$, $R^{15}$, $R^{16}$, $R^{17}$ radicals are each independently selected from the group consisting of hydrogen, an unbranched or branched alkyl group having 1 to 30 carbon atoms, and a group having the chemical structure (x)

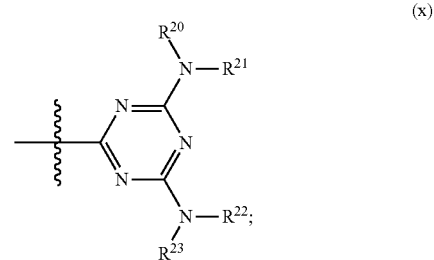

(x)

wherein the $R^{18}$, $R^{19}$, $R^{20}$, $R^{21}$, $R^{22}$, $R^{23}$ radicals are each independently selected from the group consisting of hydrogen, unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, and —N(CH)(CH$_2$CH$_3$), and a radical having a chemical structure (xvii)

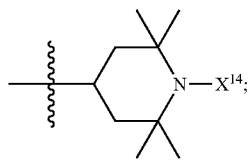

(xvii)

wherein $X^{14}$ is selected from the group consisting of hydrogen, —OH, —O., unbranched or branched alkyl group having 1 to 10 carbon atoms, and unbranched or branched alkoxy group having 1 to 10 carbon atoms, and with the proviso that $R^{12}$ and $R^{17}$, if $p^{13}=p^{14}=p^{15}=p^{16}=0$, are each independently selected from the list above including a group of the chemical structure (xviii)

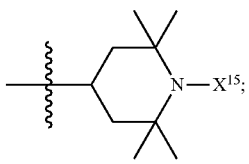

(xviii)

wherein $X^{15}$ is selected from the group consisting of hydrogen, OH, —O., unbranched or branched alkyl group having 1 to 10 carbon atoms, and unbranched or branched alkoxy group having 1 to 10 carbon atoms.

5. The process according to claim 1, wherein $X^1=X^2=X^3=X^4=X^5=X^6=X^7=X^8=X^9=X^{10}=X^{11}=X^{12}=X^{13}=X^{14}=X^{15}$=hydrogen.

6. The process according to claim 1, wherein the triacetonediamine compound (1) is selected from the group consisting of the chemical structures (I-A), and (I-B) and wherein the $R^1$, $R^2$ radicals are each independently selected from the group consisting of hydrogen, an unbranched alkyl group which has 1 to 12 carbons, and a branched alkyl group which has 1 to 12 carbon atoms, wherein at least one hydrogen radical of the branched and unbranched alkyl group may optionally be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, and —N(CH)(CH$_2$CH$_3$).

7. The process according to claim 6, wherein the triacetonediamine compound (I) is selected from the group consisting of the chemical structures (I-A), and (I-B) and wherein the $R^1$, $R^2$ radicals are each independently selected from the group consisting of hydrogen, an unbranched alkyl group having 1 to 12 carbon atoms and a branched alkyl group having 1 to 12 carbon atoms.

8. The process according to claim 1, wherein $Z^1$, $Z^2$, $Z^3$ are each independently selected from the group consisting of direct bond, an unbranched alkylene group having 1 to 30 carbon atoms, a branched alkylene group having 1 to 30 carbon atoms, and a divalent saturated hydrocarbyl group having 3 to 30 carbon atoms and having at least one saturated ring comprising 3 to 30 carbon atoms.

9. The process according to claim 1, wherein the carbonyl compound (II) is selected from the group consisting of the chemical structures (II-A), and (II-B).

10. The process according to claim 1, wherein the triacetonediamine compound (1) is selected from the group consisting of the chemical structures (I-A), and (I-B) and wherein the carbonyl compound (II) is selected from the group consisting of the chemical structures (II-A), and (II-B), wherein
$p^1=p^2=0$;
$X^1=X^2=X^3$=hydrogen;
$Y^1$ and $Z^1$ are each independently an unbranched or branched alkylene group having 1 to 12 carbon atoms;
$R^1$, $R^2$ are each independently selected from the group consisting of hydrogen, an unbranched alkyl group having 1 to 12 carbon atoms and a branched alkyl group having 1 to 12 carbon atoms;
$R^{24}$, $R^{25}$, $R^{26}$, $R^{27}$ are selected from the group consisting of hydrogen, and an unbranched alkyl group having 1 to 12 carbon atoms and a branched alkyl group having 1 to 12 carbon atoms;
wherein $R^{24}$, $R^{25}$, $R^{26}$, $R^{27}$ are each selected independently, with the exclusion of: $R^{24}=R^{25}$=hydrogen.

11. The process according to claim 10, wherein the triacetonediamine compound (I) has the chemical structure (I-A) and wherein the carbonyl compound (II) has the chemical structure (II-A), where
$X^1$=hydrogen;
$R^1$ is selected from the group consisting of hydrogen, an unbranched alkyl group having 1 to 8 carbon atoms and a branched alkyl group having 1 to 8 carbon atoms;
$R^{24}$, $R^{25}$ are selected from the group consisting of hydrogen, an unbranched alkyl group having 1 to 8 carbon atoms and a branched alkyl group having 1 to 8 carbon atoms;
wherein $R^{24}$, $R^{25}$ are each selected independently, with the exclusion of: $R^{24}=R^{25}$=hydrogen.

12. The process according to claim 11, wherein the triacetonediamine compound (I) has the chemical structure (I-A) and wherein the carbonyl compound (II) has the chemical structure (II-A), wherein $X^1$=H; $R^1$=H; $R^{24}$ is selected from the group consisting of hydrogen, and methyl; $R^{25}$ is an unbranched or branched alkyl group having 1 to 8 carbon atoms.

13. The process according to claim 1, which is conducted in at least one solvent, wherein the solvent is selected from the group consisting of aliphatic solvents, aromatic solvents, ethers, halogenated solvents, amides, thio compounds, carboxylic acids, alcohols, and water.

14. The process according to claim 1, which is conducted at a temperature in the range from 20° C. to 350° C. and a pressure in the range from 2 bar to 500 bar.

* * * * *